US009555073B2

(12) United States Patent
Ficht et al.

(10) Patent No.: US 9,555,073 B2
(45) Date of Patent: Jan. 31, 2017

(54) USE OF VITELLINE PROTEIN B AS A MICROENCAPSULATING ADDITIVE

(75) Inventors: Allison R. Ficht, College Station, TX (US); Ken Carson, Bryan, TX (US); Cynthia Sheffield, College Station, TX (US); John Herbert Waite, Santa Barbara, CA (US)

(73) Assignees: THE TEXAS A&M UNIVERSITY SYSTEM, College Station, TX (US); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 13/407,427

(22) Filed: Feb. 28, 2012

(65) Prior Publication Data

US 2012/0156287 A1 Jun. 21, 2012

Related U.S. Application Data

(62) Division of application No. 11/015,734, filed on Dec. 17, 2004, now abandoned.

(60) Provisional application No. 60/530,721, filed on Dec. 18, 2003.

(51) Int. Cl.
| | |
|---|---|
| *C07K 16/02* | (2006.01) |
| *C12N 15/00* | (2006.01) |
| *A61K 38/17* | (2006.01) |
| *A61K 9/16* | (2006.01) |
| *A61K 9/50* | (2006.01) |
| *A61K 39/00* | (2006.01) |
| *A61K 38/00* | (2006.01) |

(52) U.S. Cl.
CPC ............. *A61K 38/17* (2013.01); *A61K 9/1652* (2013.01); *A61K 9/1658* (2013.01); *A61K 9/5052* (2013.01); *A61K 39/0003* (2013.01)

(58) Field of Classification Search
None
See application file for complete search history.

(56) References Cited

U.S. PATENT DOCUMENTS

| | | | |
|---|---|---|---|
| 4,340,588 A * | 7/1982 | Woodard | 424/252.1 |
| 5,700,909 A * | 12/1997 | O'Brien | C07K 14/47 530/326 |
| 5,879,712 A * | 3/1999 | Bomberger et al. | 424/489 |
| 6,746,635 B2 | 6/2004 | Mathiowitz et al. | |
| 2002/0053544 A1* | 5/2002 | Huang et al. | 210/650 |
| 2003/0087954 A1* | 5/2003 | Palepu et al. | 514/449 |
| 2004/0028647 A1* | 2/2004 | Zagury et al. | 424/85.1 |
| 2005/0260258 A1 | 11/2005 | Ficht et al. | |
| 2006/0018918 A1* | 1/2006 | Chang | 424/185.1 |
| 2010/0184950 A1* | 7/2010 | Lee et al. | 530/324 |

OTHER PUBLICATIONS

Ain et al. (2003) Alginate-based oral drug delivery system for tuberculosis: pharmacokinetics and therapeutic effects, J. Antimicrob. Chemother., vol. 51, pp. 931-938.*
Hitchens et al. (Dec. 2002) Annual Rept, "Orally Administered Bioadherent Sustained Release Microencapsulated Vaccines", pp. 1-31.*
Migneault et al. (2004) Glutaraldehyde: behavior in aqueous solution, reaction with proteins, and application to enzyme crosslinking, Biotechniques, vol. 37, Noi.5, pp. 790-802.*
Liu et al. (2006) Chemistry of periodate-mediated cross-linking of 3,4-dihydroxylphenylalanine-containing molecules to proteins, J. Am. Chem. Soc., vol. 128, No. 47, pp. 15228-15235.*
Rice-Fitch et al. (1992) Eggshell precursor proteins of Fasciola hepatica, I. Structure and expression of vitelline protein B, Mol. Biochem. Parasitol., vol. 54, No. 2, pp. 129-141.*
Tang et al. (2005) Molecular Cloning and Characterization of Vitelline Precursor Protein B1 From Clonorchis Sinensis, J. Parasitol., vol. 91, No. 6, pp. 1374-1378.*
Arenas-Gamboa, Angela M., et al., "Immunization with a Single dose of a Microencapsuiateci *Brucella melitensis* Mutant Enhances Protection against Wild-Type Challenge," Infection and Immunity, Jun. 2008, p. 2448-2455.
Ficht, Allison, et al., "Progress Report," Jun. 30, 1990.
"File List," Published by: American Society for Microbiology, (2009).
Giletto, Anthony, "Biodegradable Bioadherent Microcapsules for Orally Administered Sustained Release Vaccines," May 1997, Annual-Phase II (Apr. 29, 1996-Apr. 28, 1997), Report AD No. ADB226038.
Hwang, D. S., et al, "Expression of Functional Recombinant Mussel Adhesive Protein Mgfp-5 in *Escherichia coli*," Applied and Environ Micro (2004), 70:3352-3359.
Morozova, E.V., et al., "RAPD Variation in Two Tremode Species (*Fascila hepatica* and *Dicrocoelium dendriticum*) from a Single Cattle Population," Russian Journal of Genetics, vol. 88, No. 8, 2002, pp. 977-983.
Rebelatto, M.C., et al., "Induction of systemic and mucosal immune response in cattle by intranasal administration of pig serum albumin in alginate mioropartioles," Veterinary Immunology and immunopathology 83 (2001) 93-105.
Arnow, L. Earle, "Colorimetric Determination of the Components of 3,4-Dihydroxyphenylalanine-Tyrosine Mixtures" Laboratory of Physiological Chemistry, University of Minnesoty, Minnepolis, Jan. 14, 1937.
Bahukudumbi, P., et al, "On the Diameter and Size Distributions of Bovine Serum Albumin (BSA)-based Microspheres," J. Microencapsulation, Nov. 2004, vol. 21, No. 7, 787-803.
Bordier, Clement, "Phrase Separation of Integral Membrane Proteins in Triton X-114 Solution," The Journal of Biological Chemistry, Feb. 25, 1981, vol. 256, No. 4, pp. 1604-1607.
Duckworth, Harry W., et al, "Physicochemical and Kinetic Properties of Mushroom Tyrosinase," The Journal of Biological Chemistry, Apr. 10, 1970, vol. 245, No. 7, pp. 1613-1625.

(Continued)

*Primary Examiner* — Anand Desai
*Assistant Examiner* — Samuel Liu
(74) *Attorney, Agent, or Firm* — Edwin S. Flores; Daniel J. Chalker; Chalker Flores, LLP

(57) ABSTRACT

The present invention includes compositions and methods for the use of an encapsulation additive having between about 0.1 to about 30 percent isolated and purified vitelline protein B to provide for mixed and extended release formulations.

11 Claims, 4 Drawing Sheets

(56) References Cited

OTHER PUBLICATIONS

Gyllensten, Ulf B., et al, "Generation of Single-Stranded DNA by the Polymerase Chain Reaction and its Application to Direct Sequencing of the HLA-DQA Locus," Proc. Natl. Acad. Sci., Oct. 1988, Vo. 85, pp. 7652-7656.

Qurrat-Ul-Ain, et al, "Alginate-based Orak Drug Delivery System of Tuberculosis: Pharmacokinetics and Therapeutic Effects," Journal of Antimicrobial Chemotherapy, 2003, 51, 931-938.

Rice-Ficht, Allison C., et al, "Eggshell Precursor of Fasciola Hepatica, I. Structure and Expression of Vitelline Protein B," Molecular and Biochemical Parasitology, 1992, 54, 129-142, Elsevier Science Publishers B.V.

Waite, J. H., "Presclero Eggshell Protein from the Liver Fluke Fasciola hepatica," Biochemistry, 1987, 26, 7819-7825.

Waite, J. H., "A Histidine-Rich Protein from the Vitellaria of the Liver Fluke *Fasciola hepatica*," Biochemistry, 1989, 28, 6104-6110.

Waite, J. H., "Eggshell Precursor Proteins of Fasciola hepatica. II. Microheterogeneity in Vitelline Protein B." Molecular and Biochemical Parasitology, 1992, 54, 143-152.

\* cited by examiner

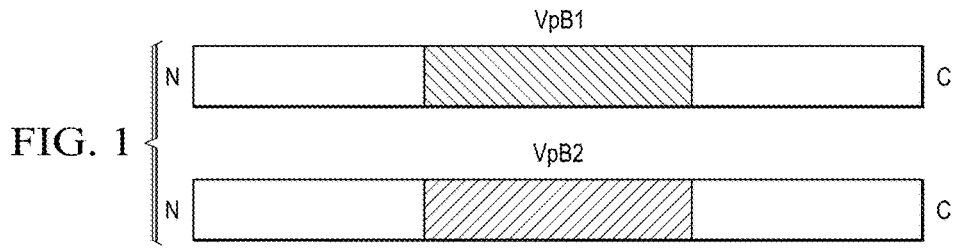
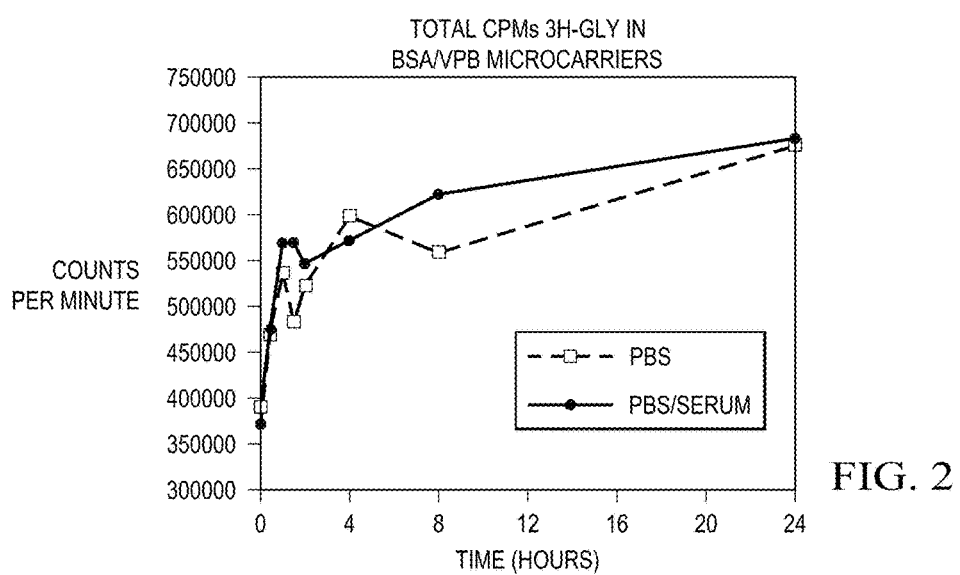
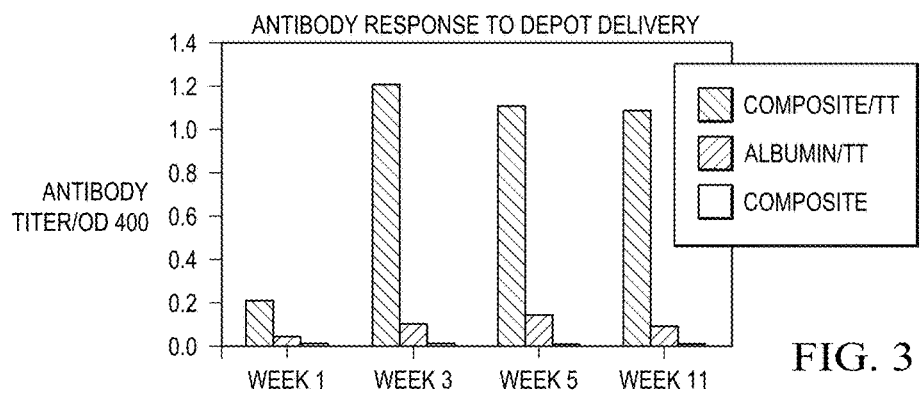
FIG. 1
FIG. 2
FIG. 3

SEQUENCE LISTING

```
<160> NUMBER OF SEQ ID NOS: 2

<210> SEQ ID NO 1
<211> LENGTH: 252
<212> TYPE: PRT
<213> ORGANISM: Artificial Sequence
<220> FEATURE:
<223> OTHER INFORMATION: Synthetic peptide

<400> SEQUENCE: 1

Met Lys Met Lys Phe Thr Leu Val Leu Leu Leu Ala Ile Val Pro Leu
1               5                   10                  15

Thr Leu Ala Arg His Pro His Gly Lys Phe Asn Arg His Ala Ser Tyr
            20                  25                  30

Asp Asp Arg Phe Lys His Arg Gly Tyr Arg Lys Glu Asn Asp Leu Asn
        35                  40                  45

Asp Leu Lys Gly Lys Phe Ala Gly Arg Gly Lys Ala Leu His Gly Ser
    50                  55                  60
```

-continued

```
Phe Asp Lys Tyr Gly Asn Glu Asn Glu Arg Gly Arg Tyr Asp Asp Gln
 65                  70                  75                  80

Gly Lys Tyr Leu Leu Ala Gly Lys Ser Ala His Asp Gly Lys Tyr Gly
                 85                  90                  95

Met Tyr Gly Asn Met Tyr Ala Lys Gly Asp Phe Lys Ala Tyr Gly Asn
            100                 105                 110

Glu Asp Glu Gly Ala Lys Phe Glu Glu Val Thr Thr Phe Arg Arg Gly
        115                 120                 125

Gly Gly Asp Ser Gly Lys Lys Lys Ser Asp Asp Thr Lys Gly His
    130                 135                 140

Leu Lys Lys Phe Ala Asn Lys Gly Arg Gln Ser Lys Phe Asp Met Gly
145                 150                 155                 160

Asn Val Lys Ala Asp Gly Gln Ala Ile Ser Asn Gly Asn Met Asn Ala
                165                 170                 175

Gly Met Phe Asp Ser Gly Lys Asp Gln Gly Lys Met Asn Asp Gln Gly
            180                 185                 190

Lys Glu Glu Ala Gly Lys Tyr Asn Ala His Gly Asn Leu Asp Leu Tyr
        195                 200                 205

Gly His Leu Arg Gly Gly Ser Ser Ala Ala Ser Lys Ser Glu Asn
    210                 215                 220

Tyr Gly Asn Ala Arg Glu Ser Gly Arg Glu Pro Gly Arg Tyr Glu Lys
225                 230                 235                 240

Glu Asp Asp Ala Arg Glu Thr Pro Tyr Asp Lys Ser
                245                 250

<210> SEQ ID NO 2
<211> LENGTH: 253
<212> TYPE: PRT
<213> ORGANISM: Artificial Sequence
<220> FEATURE:
<223> OTHER INFORMATION: Synthetic peptide

<400> SEQUENCE: 2

Met Lys Met Lys Phe Thr Leu Val Leu Leu Ala Ile Val Pro Leu
 1               5                  10                  15

Thr Leu Ala Arg His Pro His Gly Lys Phe Asn Arg His Ala Ser Tyr
                 20                  25                  30

Asp Asp Arg Phe Lys His Arg Gly Tyr Arg Lys Glu Asn Asp Leu Asn
            35                  40                  45

Asp Leu Lys Gly Lys Phe Ala Gly His Gly Lys Ala Leu His Gly Ser
        50                  55                  60

Phe Asp Lys Tyr Gly Asn Glu Asn Glu Arg Gly Arg Tyr Asp His Arg
 65                  70                  75                  80

Gly His His Ser Leu Ala Val Lys Ser Ala His Asp Gly Lys Tyr Asp
                 85                  90                  95

Met Tyr Gly Arg Met Tyr Ala Lys Ala Asn Phe Asp Ala His Gly His
            100                 105                 110

Glu Lys Glu Gly Thr Lys Phe Glu Glu Val Thr Lys Phe Arg Arg Gly
        115                 120                 125

Gly Gly Gly Gly Lys Lys Lys Ser Asp Asp Thr Lys Gly His
    130                 135                 140

Met Lys Arg Phe Ala Asp Lys Gly Met Lys Ser Lys Phe Asp Leu Gly
145                 150                 155                 160

Asn Val Glu Ala Lys Gly Lys Ala Asp Ala Asn Gly Lys Met Gly Ala
                165                 170                 175
```

-continued

```
Leu Gly Lys Phe Asp Ser Gly Lys Asp Gln Gly Lys Met Asn Asp Gln
            180                 185                 190

Gly Lys Glu Glu Ala Gly Lys Tyr Asn Ala His Gly Asn Leu Asp Leu
        195                 200                 205

Tyr Gly His Leu Arg Gly Gly Gly Ser Ser Ala Ala Ser Lys Ser Glu
    210                 215                 220

Asn Tyr Gly Asn Ala Arg Glu Ser Gly Arg Glu Pro Gly Arg Tyr Glu
225                 230                 235                 240

Lys Glu Asp Asp Ala Arg Glu Thr Pro Tyr Asp Lys Ser
                245                 250
```

USE OF VITELLINE PROTEIN B AS A MICROENCAPSULATING ADDITIVE

CROSS-REFERENCE TO RELATED APPLICATIONS

This application is a divisional of U.S. Ser. No. 11/015,734, filed on Dec. 17, 2004, entitled "Use of Vitelline Protein B as a Microencapsulating Additive", by inventors Ficht, et al., currently pending, which claims benefit under 35 U.S.C. §119(e) of provisional application U.S. Ser. No. 60/530,721, filed Dec. 18, 2003. The contents of which are incorporated by reference herein in their entirety.

STATEMENT REGARDING FEDERALLY SPONSORED RESEARCH

The government may own rights in the present invention pursuant to grant number NCC-1-02038 from the National Aeronautics and Space Administration (NASA); contract #0300125 from the US Geological Survey, Department of the Interior, National Park Service; and contract#DAMD17-95-C-5048 from the U.S. Army Medical Research and Materiel Command.

FIELD OF THE INVENTION

The invention relates to compositions and methods for extended release encapsulation using additives, and more particularly, to vitelline proteins as microencapsulation additives and uses thereof.

INCORPORATION-BY-REFERENCE OF MATERIALS FILED ON COMPACT DISC

The present application includes a Sequence Listing which has been submitted in ASCII format via EFS-Web and is hereby incorporated by reference in its entirety. Said ASCII copy, created on Jul. 26, 2016, is named TAMU1006_seq_listing.txt and is 5K bytes in size.

BACKGROUND OF THE INVENTION

Without limiting the scope of the invention, its background is described in connection with polymeric encapsulation of compounds.

The encapsulation of pharmaceuticals and other compounds is of continuing interest, both in industry and in academia. Encapsulation may be used to modify the time-release properties of a material, to alter the solubility of a material and/or to provide other desirable property modifications. Polymers, biopolymers and peptides have been explored for their suitability as microencapsulation agents.

Microcapsules include, generally, a core material (liquid or solid) encased in a specialized coating. Microencapsulation technology has found widespread use in the pharmaceutical area, for example, coating of drugs to extend or delay their release or target their release to a specific area of the digestive tract. Other interesting applications include encapsulation of ink in carbonless carbon paper, encapsulation of perfumes in 'scratch and sniff' types of promotionals and encapsulation of living pancreatic cells to treat diabetes. In the case of living cells, the pore size of the microcapsule is selected to prevent the passage of host antibodies while allowing the free exchange of insulin and glucagon. Microcapsules have also found application in the food, cleaning, adhesives, fertilizers and aerospace industries to name a few.

Albumin has been used in the preparation of microcapsules. Two technologies have been used—coacervation, or oil in water emulsions. These techniques have been the source of many publications, including Zimmer et al. (J. Controlled Release 33: 31-46 (1995)); Cremers et al. (Biomaterials 15(1): 38-48 (1994)); Deasy (Microencapsulation and Related Drug Processes; Marcel Dekker, Inc., NY (1984)); and Tomlinson, E. and Burger, J. J. *Methods Enzymol.* 112: 27-43 (1985)). Despite the efforts made towards developing microencapsulation methods, there still exists a need for novel and effective materials for the encapsulation of various materials.

SUMMARY OF THE INVENTION

The compositions and methods of the present invention include, generally, an encapsulation additive comprising between about 0.1 to about 30 percent isolated and purified vitelline protein B. The present inventors recognized that a key aspect of trematode infection and survival is the avoidance of host immune responses. Studies as to the causes for evasion of host immune surveillance led to the isolation and characterization of proteins from trematode eggshells. Upon isolation of the genes for the trematode proteins, vitelline protein A (vpA), vitelline protein B (vpB) and vitelline protein C (vpC) and isoforms of the same, it was discovered, as disclosed herein that the vpB protein, in particular, is stable at a wide range of pHs, is protease resistant and non-immunogenic. As such, the present investigators used the vpB protein as an additive for the encapsulation and extended release of, small molecules, antigens and the like.

More particularly, the encapsulation additive of the present invention may include the vitelline protein B from a Trematode sp. The additive is generally non-antigenic, is resistant to acid and base pH or both and may allow for the slow release of an active agent to between about 1 hour to about to about 8 hours, between about 1 hour to about 2 weeks, and between about 1 hour to about 6 months. Examples of the one or more active agents may include a pharmaceutical agent, an enzyme, a cytokine, a growth promoting agent, an antibody, an antigen, a vaccine, a cell, a live-attenuated pathogen, a heat-killed pathogen, a virus, a bacteria, a fungi, a peptide, a carbohydrate, a nucleic acid, a lipid, mixtures and combinations thereof. The vitelline protein B may be formed into a capsule when combined by coacervation, added into an oil-and-water emulsion, liposomes, spray freezing, spray drying, as a component of an alginate microcapsule or combinations thereof. Other examples of active agents include: protein, peptide, carbohydrate, polysaccharide, glycoprotein, lipid, hormone, growth factor, cytokine, interferon, receptor, antigen, allergen, antibody, substrate, metabolite, cofactor, inhibitor, drug, pharmaceutical, nutrient, toxin, poison, explosive, pesticide, chemical warfare agent, biowarfare agent, biohazardous agent, infectious agent, prion, radioisotope, vitamin, heterocyclic aromatic compound, carcinogen, mutagen, narcotic, amphetamine, barbiturate, hallucinogen, waste product, contaminant, heavy metal, virus, bacterium, *Salmonella, Streptococcus, Brucella, Legionella, E. coli, Giardia, Cryptosporidium, Rickettsia*, spore, mold, yeast, algae, amoebae, dinoflagellate, unicellular organism, pathogen, cell, combinations and mixtures thereof, that is encapsulated in a mixed release polymer comprising between about 0.1 to about 26, about 0.1 to about 30, or even about 0.1 to about 90 weight percent isolated and purified recombinant vitelline protein B.

Yet another embodiment of the present invention may be a mixed release pharmaceutical formulation with one or more active agents microencapsulated in a mixed release polymer and between about 0.1 to 26 percent isolated and purified vitelline protein B. A polymer selected from the group consisting of cellulose, ethylcellulose, methylcellulose, propylcellulose, methoxypropylcellulose, cellulose nitrate, poly(vinyl alcohol), poly(vinyl chloride), polystyrene, polyethylene, polypropylene, poly(ethylene-co-vinyl acetate), poly(hydroxybutyric acid), poly(hydroxyvalerianic acid-co-hydroxybutyric acid), poly(lactic acid), poly(glycolic acid), poly(lactic acid-co-glycolic acid), poly(epsilon (-caprolactones), poly(epsilon(-caprolactone-co-DL-lactic acid), poly(maleic anhydride), polyamides, gelatin, chitosan, collagen, poly(hydroxyalkyl)-L-glutamines, poly(gamma(-ethyl-L-glutaminate-co-glutamic acid), poly(L-leucine-co-L-aspartic acid), poly(proline-co-glutamic acid), poly(alkyl 2-cyanoacrylates), polyurethanes, poly(methyl methacrylate), poly(methyl methacrylate-co-methacrylic acid) and poly(methacrylate-co-hydroxypropyl methacrylate).

Other examples of active agents may include a pharmaceutical agent, an enzyme, a cytokine, a growth promoting agent, an antibody, an antigen, a vaccine, a cell, a live-attenuated pathogen, a heat-killed pathogen, a virus, a bacteria, a fungi, a peptide, a carbohydrate, a nucleic acid, a lipid, mixtures and combinations thereof.

The present invention may also include a method of encapsulation that includes the steps of mixing one or more active agents with one or more cross-linkable monomers and a vitelline protein B, wherein the vitelline protein B modifies the release profile of the one or more active agents. Alternatively, the method of making an extended release formulation may include the steps of mixing one or more active agents with alginate and vitelline protein B, wherein the vitelline protein B modifies the release profile of one or more of the active agents. The one or more active agents are released for between about 1 hour to about 8 hours, between about 1 hour to about 2 weeks, and between about 1 hour to about 6 month and the vitelline protein B comprises a Trematode sp. protein that is non-antigenic, is resistant to acid pH, resistant to basic pH or combinations thereof. The method may also include the step of mixing poly-L lysine with the vitelline protein B, wherein the ratio of the poly-L lysine to vitelline protein B is between about 30:70 to 70:30 weight to weight.

Yet another embodiment of the present invention is a mixed release pharmaceutical formulation in which one or more one or more pharmaceutical agents is encapsulated in a mixed release polymer comprising between about 0.1 to 26 weight percent isolated and purified vitelline protein B. Examples of pharmaceutical agents include: steroids, respiratory agents, sympathomimetics, local anesthetics, antimicrobial agents, antiviral agents, antifungal agents, antihelminthic agents, insecticides, antihypertensive agents, antihypertensive diuretics, cardiotonics, coronary vasodilators, vasoconstrictors, β-blockers, antiarrhythmic agents, calcium antagonists, anti-convulsants, agents for dizziness, tranquilizers, antipsychotics, muscle relaxants, drugs for Parkinson's disease, respiratory agents, hormones, non-steroidal hormones, antihormones, vitamins, antitumor agents, miotics, herb medicines, antimuscarinic, interfereons, immunokines, cytokines, muscarinic cholinergic blocking agents, mydriatics, psychic energizers, humoral agents, antispasmodics, antidepressant drugs, anti-diabetics, anorectic drugs, anti-allergenics, decongestants, expectorants, antipyretics, antimigrane, anti-malarials, anti-ulcerative, peptides, anti-estrogen, anti-hormone agents, antiulcer agents, anesthetic agent, drugs having an action on the central nervous system or combinations thereof. The polymer may be a biocompatible and/or biodegradable polymer selected from: poly(ethylene glycol), poly(ethylene oxide), poly(vinyl alcohol), poly(vinylpyrrolidone), poly(ethyloxazoline), poly(ethylene oxide)-co-poly(propylene oxide) block copolymers, polysaccharides, carbohydrates, proteins and combinations thereof.

A mixed release pharmaceutical formulation using the vpB additive of the present invention may include one or more active agents selected from protein, peptide, carbohydrate, polysaccharide, glycoprotein, lipid, hormone, growth factor, cytokine, interferon, receptor, antigen, allergen, antibody, substrate, metabolite, cofactor, inhibitor, drug, pharmaceutical, nutrient, toxin, poison, explosive, pesticide, chemical warfare agent, biowarfare agent, biohazardous agent, infectious agent, prion, radioisotope, vitamin, heterocyclic aromatic compound, carcinogen, mutagen, narcotic, amphetamine, barbiturate, hallucinogen, waste product, contaminant, heavy metal, virus, bacterium, *Salmonella, Streptococcus, Brucella, Legionella, E. coli, Giardia, Cryptosporidium, Rickettsia*, spore, mold, yeast, algae, amoebae, dinoflagellate, unicellular organism, pathogen, cell, combinations and mixtures thereof, that is encapsulated in a mixed release polymer and between about 0.1 to 26 weight percent isolated and purified vitelline protein B.

Yet another embodiment of the present invention is a vaccine in which one or more antigens are encapsulated in a mixed release with between about 0.1 to 26 weight percent isolated and purified vitelline protein B. The antigen may be selected from: protein, peptide, carbohydrate, polysaccharide, glycoprotein, lipid, hormone, growth factor, cytokine, interferon, receptor, antigen, allergen, antibody, substrate, metabolite, cofactor, inhibitor, drug, pharmaceutical, nutrient, toxin, poison, explosive, pesticide, chemical warfare agent, biowarfare agent, biohazardous agent, infectious agent, prion, radioisotope, vitamin, heterocyclic aromatic compound, carcinogen, mutagen, narcotic, amphetamine, barbiturate, hallucinogen, waste product, contaminant, heavy metal, virus, bacterium, *Salmonella, Streptococcus, Brucella, Legionella, E. coli, Giardia, Cryptosporidium, Rickettsia*, spore, mold, yeast, algae, amoebae, dinoflagellate, unicellular organism, pathogen, cell, combinations and mixtures thereof. Yet another embodiment of the present invention is an adhesive having between about 1 to about 90 percent isolated and purified vitelline protein B.

The vpB additive and methods disclosed herein may be used for the micro and nano-encapsulation of a number of active agents, e.g., peptides, proteins, aptamers, oligonucleotides, carbohydrates, lipids, glycolipids, glycoproteins, anti-obesity drugs, nutraceuticals, corticosteroids, elastase inhibitors, analgesics, anti-fungals, antibiotics, antibodies, antigens, oncology therapies, anti-emetics, analgesics, cardiovascular agents, anti-inflammatory agents, antigens, anti-helmintics, anti-arrhythmic agents, antibiotics, antibodies, anticoagulants, antidepressants, antidiabetic agents, antiepileptics, antihistamines, antihypertensive agents, antimuscarinic agents, antimycobacterial agents, antineoplastic agents, immunosuppressants, antithyroid agents, antiviral agents, anxiolytics, sedatives, astringents, beta-adrenoceptor blocking agents, blood products and substitutes, cardiac inotropic agents, contrast media, corticosteroids, cough suppressants, diagnostic agents, diagnostic imaging agents, diuretics, dopaminergics, haemostatics, immunological agents (cytokines, lymphokines), lipid regulating agents, muscle relaxants, parasympathomimetics, parathyroid calcitonin and biphosphonates, prostaglandins, radio-pharmaceuticals, sex hormones, insecticides, anti-allergic agents, stimulants and anoretics, sympathomimetics, thyroid agents, vasodilators, and xanthines, and derivatives, salts and combinations thereof. The skilled artisan will recognize that a number of agents may be used and/or delivered in combination with the present invention, including, organic or inorganic molecules (small or large), second messengers, nucleic acids (natural, non-natural and derivatives thereof), amino acids (natural, non-natural and derivatives thereof), carbohydrates (monomeric or oligomeric), lipids, cells, cell fragments, glycoproteins, nutrients, vitamins, etc.

The vpB and related proteins of the present invention may also be used in a method of treating an animal, the method in which the mixed release formulation of the present invention is administered to a mammal. In an alternative embodiment, the vpB protein may also be used as a bent core mesogen piezoelectric component.

BRIEF DESCRIPTION OF THE FIGURES

For a more complete understanding of the features and advantages of the present invention, reference is now made to the detailed description of the invention along with the accompanying figures and in which:

FIG. 1 is a map that summarizes the divergence of amino acid sequence between vpB family members: hatched lines indicate areas of highly divergent amino acid sequence;

FIG. 2 is a graph that shows the release of a small molecule, [3H] glycine, encapsulated using the additive of the present invention;

FIG. 3 is a graph that shows the antibody titer of mice treated via subcutaneous injection of encapsulated tetanus toxoid;

DETAILED DESCRIPTION OF THE INVENTION

Figure 4:
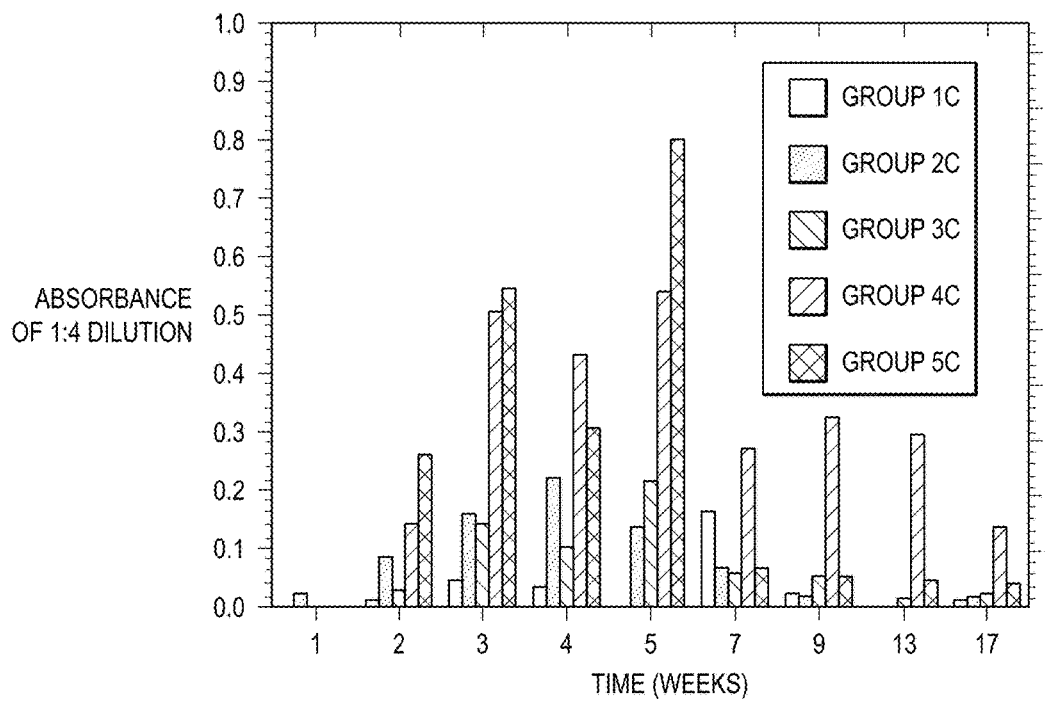
FIG. 4 is a graph that shows the antibody titer of mice treated via subcutaneous injection with botulinum toxin encapsulated using the present invention and delivered as a depot.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The term "additive" as used herein is used to describe vpB protein, variants thereof, and proteins and peptides that have a similar protein composition to produce encapsulants that affect the release of an agent trapped in or about the additive, e.g., when the additive is mixed with a polymeric or other composition to form a micro or nanocapsule. It has been found, as described in detail hereinbelow, that the Vitelline protein B is a member of a family of proteins with variable sequences, however, the amino acid composition is fixed. The Vitelline protein B may be closed and/or isolated by purification from, e.g., *Fasciola hepatica*. Alternatively, the Vitelline protein B may be made synthetically, by recombinant methods and combinations thereof.

The term "immediate release" as used herein is used to describe a release profile to effect delivery of an active as soon as possible, that is, as soon as practically made available to an animal, whether in active form, as a precursor and/or as a metabolite. Immediate release may also be defined functionally as the release of over 80 to 90 percent (%) of the active ingredient within about 60, 90, 100 or 120 minutes or less.

The terms "extended release" and "delayed release" as used herein is used to define a release profile to effect delivery of an active over an extended period of time, defined herein as being between about 60 minutes and about 2, 4, 6 or even 8 hours. Extended release may also be defined functionally as the release of over 80 to 90 percent (%) of the active ingredient after about 60 minutes and about 2, 4, 6 or even 8 hours. Extended release as used herein may also be defined as making the active ingredient available to the patient or subject regardless of uptake, as some actives may never be absorbed by the animal. Various extended release dosage forms may be designed readily by one of skill in art as disclosed herein to achieve delivery to both the small and large intestines, to only the small intestine, or to only the large intestine, depending upon the choice of coating materials and/or coating thickness.

"Extended release" and "delayed release" formulations may be prepared and delivered using the Vitelline protein B or variants thereof to control the release of an agent. The Vitelline protein B protein may act alone or in combination with other compounds that delay release of an active, e.g., a coating, a capsule or mixture with controlled, delayed or extended release polymers. Any coatings should be applied to a sufficient thickness such that the entire coating does not dissolve in the gastrointestinal fluids at pH below about 5, but does dissolve at pH about 5 and above. It is expected that any anionic polymer exhibiting a pH-dependent solubility profile can be used as an enteric coating in the practice of the present invention to achieve delivery to the lower gastrointestinal tract. Polymers and compatible mixtures thereof may be used to provide the coating for the delayed or the extended release of active ingredients, and some of their properties, include, but are not limited to: shellac, also called purified lac, a refined product obtained from the resinous secretion of an insect. This coating dissolves in media of pH>7.

As used herein, the term "enveloped pharmaceutical" means a capsule, a suppository, a gel cap, a softgel, a lozenge, a sachet or even a fast dissolving wafer. As used herein the term "carrier" is used to describe a substance, whether biodegradable or not, that is physiologically acceptable for human or animal use and may be pharmacologically active or inactive.

The vpB additive of the present invention may be used in conjunction with a wide variety of dosage forms, e.g., solution, suspension, cream, ointment, lotion, capsule, caplet, softgel, gelcap, suppository, enema, elixir, syrup, emulsion, film, granule, gum, insert, jelly, foam, paste, pastille, pellet, spray, troche, lozenge, disk, magma, poultice, or wafer and the like.

The vpB additive of the present invention may be used to delivery active pharmaceutical agents. As used herein, "pharmaceutically" and/or "pharmacologically acceptable" refer to molecular entities and/or compositions that do not produce an adverse, allergic and/or other untoward reaction when administered to an animal, as appropriate. One distinct advantage of vpB is that it does not generally cause an adverse, allergic and/or other untoward reaction when administered to an animal.

As used herein, "pharmaceutically acceptable carrier" may include any and/or all solvents, dispersion media, coatings, antibacterial and/or antifungal agents, isotonic and/or absorption delaying agents and/or the like. The use of such media and/or agents for pharmaceutical active substances is well known in the art. Except insofar as any conventional media and/or agent is incompatible with the active ingredient, its use in the therapeutic compositions is contemplated. Supplementary active ingredients can also be incorporated into the compositions. For administration, preparations should meet sterility, pyrogenicity, general safety and/or purity standards as required by FDA Office of Biologics standards.

As used herein, the term "therapeutically effective dosage" is used to describe the amount that reduces the amount of symptoms of the condition in the infected subject by at least about 20%, more preferably by at least about 40%, even more preferably by at least about 60%, and still more preferably by at least about 80% relative to untreated subjects. Often, for pediatric doses the amount will be half or less of the adult dose. For example, the efficacy of a compound may be evaluated in an animal model system that may be predictive of efficacy in treating the disease in humans. Bioactive compounds are administered at a therapeutically effective dosage sufficient to treat a condition associated with a condition in a subject.

The terms "amount," "pharmaceutically effective amount" and "therapeutically effective amount" as used herein refer to a quantity or to a concentration as appropriate to the context. The amount of an active agent or drug that constitutes a pharmaceutically or therapeutically effective amount varies according to factors such as the potency of the particular drug, the route of administration of the formulation, and the mechanical system used to administer the formulation as will be known to the skilled artisan. For example, a pharmaceutically or therapeutically effective amount is that dosage of active agents that when released is sufficient to effect treatment, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art. The amount of active agent and the need and amount of carriers and/or excipients are disclosed, simply by way of example, by Remington's Pharmaceutical Sciences, 19th edition, 1995, Ed. Gennaro, relevant portions incorporated herein by reference. The term "treatment" or "treating" means any treatment of a disease in a mammal, including: (i) preventing the disease, that is, causing the clinical symptoms of the disease not to develop; (ii) inhibiting the disease, that is, arresting the development of clinical symptoms; and/or (iii) relieving the disease, that is, causing the regression of clinical symptoms.

The additive of the present invention may be used in conjunction with one or more carriers. As used herein the terms "carrier" and "pharmaceutically acceptable carrier" include any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

As used herein, the term "active ingredient(s)," "pharmaceutical ingredient(s)," "active agents" and "bioactive agent" are defined as drugs and/or pharmaceutically active ingredients. The present invention may be used to encapsulate, attach, bind or otherwise be used to affect the storage, stability, longevity and/or release of any of the following drugs as the pharmaceutically active agent in a composition.

One or more of the following bioactive agents may be combined with the vpB additive disclosed herein: Analgesic anti-inflammatory agents such as, acetaminophen, aspirin, salicylic acid, methyl salicylate, choline salicylate, glycol salicylate, l-menthol, camphor, mefenamic acid, flufenamic acid, indomethacin, diclofenac, alclofenac, ibuprofen, ketoprofen, naproxene, pranoprofen, fenoprofen, sulindac, fenbufen, clidanac, flurbiprofen, indoprofen, protizidic acid, fentiazac, tolmetin, tiaprofenic acid, bendazac, bufexamac, piroxicam, phenylbutazone, oxyphenbutazone, clofezone, pentazocine, mepirizole and the like.

Drugs having an action on the central nervous system, for example sedatives, hypnotics, antianxiety agents, analgesics and anesthetics, such as, chloral, buprenorphine, naloxone, haloperidol, fluphenazine, pentobarbital, phenobarbital, secobarbital, amobarbital, cydobarbital, codeine, lidocaine, tetracaine, dyclonine, dibucaine, cocaine, procaine, mepivacaine, bupivacaine, etidocaine, prilocalne, benzocaine, fentanyl, nicotine and the like. Local anesthetics such as, benzocaine, procaine, dibucaine, lidocaine and the like.

Antihistaminics or antiallergic agents such as, diphenhydramine, dimenhydrinate, perphenazine, triprolidine, pyrilamine, chlorcyclizine, promethazine, carbinoxamine, tripelennamine, brompheniramine, hydroxyzine, cyclizine, meclizine, clorprenaline, terfenadine, chlorpheniramine and the like. Anti-allergenics such as, antazoline, methapyrilene, chlorpheniramine, pyrilamine, pheniramine and the like. Decongestants such as, phenylephrine, ephedrine, naphazoline, tetrahydrozoline and the like.

Antipyretics such as, aspirin, salicylamide, non-steroidal anti-inflammatory agents and the like. Antimigrane agents such as, dihydroergotamine, pizotyline and the like.

Acetonide anti-inflammatory agents, such as hydrocortisone, cortisone, dexamethasone, fluocinolone, triamcinolone, medrysone, prednisolone, flurandrenolide, prednisone, halcinonide, methylprednisolone, fludrocortisone, corticosterone, paramethasone, betamethasone, ibuprophen, naproxen, fenoprofen, fenbufen, flurbiprofen, indoprofen, ketoprofen, suprofen, indomethacin, piroxicam, aspirin, salicylic acid, diflunisal, methyl salicylate, phenylbutazone, sulindac, mefenamic acid, meclofenamate sodium, tolmetin and the like. Muscle relaxants such as, tolperisone, baclofen, dantrolene sodium, cyclobenzaprine.

Steroids such as, androgenic steroids, such as, testosterone, methyltestosterone, fluoxymesterone, estrogens such as, conjugated estrogens, esterified estrogens, estropipate, 17-β estradiol, 17-β estradiol valerate, equilin, mestranol, estrone, estriol, 17β ethinyl estradiol, diethylstilbestrol, progestational agents, such as, progesterone, 19-norprogesterone, norethindrone, norethindrone acetate, melengestrol, chlormadinone, ethisterone, medroxyprogesterone acetate, hydroxyprogesterone caproate, ethynodiol diacetate, norethynodrel, 17-α hydroxyprogesterone, dydrogesterone, dimethisterone, ethinylestrenol, norgestrel, demegestone, promegestone, megestrol acetate and the like.

Respiratory agents such as, theophilline and β2-adrenergic agonists, such as, albuterol, terbutaline, metaproterenol, ritodrine, carbuterol, fenoterol, quinterenol, rimiterol, solmefamol, soterenol, tetroquinol and the like. Sympathomimetics such as, dopamine, norepinephrine, phenylpropanolamine, phenylephrine, pseudoephedrine, amphetamine, propylhexedrine, arecoline and the like.

Antimicrobial agents including antibacterial agents, antifungal agents, antimycotic agents and antiviral agents; tetracyclines such as, oxytetracycline, penicillins, such as, ampicillin, cephalosporins such as, cefalotin, aminoglycosides, such as, kanamycin, macrolides such as, erythromycin, chloramphenicol, iodides, nitrofrantoin, nystatin, amphotericin, fradiomycin, sulfonamides, purroInitrin, clotrimazole, miconazole chloramphenicol, sulfacetamide, sulfamethazine, sulfadiazine, sulfamerazine, sulfamethizole and sulfisoxazole; antivirals, including idoxuridine; clarithromycin; and other anti-infectives including nitrofurazone and the like.

Antihypertensive agents such as, clonidine, α-methyldopa, reserpine, syrosingopine, rescinnamine, cinnarizine, hydrazine, prazosin and the like. Antihypertensive diuretics such as, chlorothiazide, hydrochlorothiazide, bendoflumethazide, trichlormethiazide, furosemide, tripamide, methylclothiazide, penfluzide, hydrothiazide, spironolactone, metolazone and the like. Cardiotonics such as, digitalis, ubidecarenone, dopamine and the like. Coronary vasodilators such as, organic nitrates such as, nitroglycerine, isosorbitol dinitrate, erythritol tetranitrate, and pentaerythritol tetranitrate, dipyridamole, dilazep, trapidil, trimetazidine and the like. Vasoconstrictors such as, dihydroergotamine, dihydroergotoxine and the like. β-blockers or antiarrhythmic agents such as, timolol pindolol, propranolol and the like. Humoral agents such as, the prostaglandins, natural and synthetic, for example PGE1, PGE2α, and PGF2α, and the PGE1 analog misoprostol. Antispasmodics such as, atropine, methantheline, papaverine, cinnamedrine, methscopolamine and the like.

Calcium antagonists and other circulatory organ agents, such as, aptopril, diltiazem, nifedipine, nicardipine, verapamil, bencyclane, ifenprodil tartarate, molsidomine, clonidine, prazosin and the like. Anti-convulsants such as, nitrazepam, meprobamate, phenyloin and the like. Agents for dizziness such as, isoprenaline, betahistine, scopolamine and the like. Tranquilizers such as, reserprine, chlorpromazine, and antianxiety benzodiazepines such as, alprazolam, chlordiazepoxide, clorazeptate, halazepam, oxazepam, prazepam, clonazepam, flurazepam, triazolam, lorazepam, diazepam and the like.

Antipsychotics such as, phenothiazines including thiopropazate, chlorpromazine, triflupromazine, mesoridazine, piperracetazine, thioridazine, acetophenazine, fluphenazine, perphenazine, trifluoperazine, and other major tranquilizers such as, chlorprathixene, thiothixene, haloperidol, bromperidol, loxapine, and molindone, as well as, those agents used at lower doses in the treatment of nausea, vomiting and the like.

Drugs for Parkinson's disease, spasticity, and acute muscle spasms such as levodopa, carbidopa, amantadine, apomorphine, bromocriptine, selegiline (deprenyl), trihexyphenidyl hydrochloride, benztropine mesylate, procyclidine hydrochloride, baclofen, diazepam, dantrolene and the like. Respiratory agents such as, codeine, ephedrine, isoproterenol, dextromethorphan, orciprenaline, ipratropium bromide, cromglycic acid and the like. Non-steroidal hormones or antihormones such as, corticotropin, oxytocin, vasopressin, salivary hormone, thyroid hormone, adrenal hormone, kallikrein, insulin, oxendolone and the like.

Vitamins such as, vitamins A, B, C, D, E and K and derivatives thereof, calciferols, mecobalamin and the like for dermatologically use. Enzymes such as, lysozyme, urokinaze and the like. Herb medicines or crude extracts such as, Aloe vera and the like.

Antitumor agents such as, 5-fluorouracil and derivatives thereof, krestin, picibanil, ancitabine, cytarabine and the like. Anti-estrogen or anti-hormone agents such as, tamoxifen or human chorionic gonadotropin and the like. Miotics such as pilocarpine and the like.

Cholinergic agonists such as, choline, acetylcholine, methacholine, carbachol, bethanechol, pilocarpine, muscarine, arecoline and the like. Antimuscarinic or muscarinic cholinergic blocking agents such as, atropine, scopolamine, homatropine, methscopolamine, homatropine methylbromide, methantheline, cyclopentolate, tropicamide, propantheline, anisotropine, dicyclomine, eucatropine and the like.

Mydriatics such as, atropine, cyclopentolate, homatropine, scopolamine, tropicamide, eucatropine, hydroxyamphetamine and the like. Psychic energizers such as 3-(2-aminopropy)indole, 3-(2-aminobutyl)indole and the like.

Antidepressant drugs such as, isocarboxazid, phenelzine, tranylcypromine, imipramine, amitriptyline, trimipramine, doxepin, desipramine, nortriptyline, protriptyline, amoxapine, maprotiline, trazodone and the like. Anti-diabetics such as, insulin, and anticancer drugs such as, tamoxifen, methotrexate and the like. Anorectic drugs such as, dextroamphetamine, methamphetamine, phenylpropanolamine, fenfluramine, diethylpropion, mazindol, phentermine and the like. Anti-malarials such as, the 4-aminoquinolines, alphaminoquinolines, chloroquine, pyrimethamine and the like. Antiulcerative agents such as, misoprostol, omeprazole, enprostil and the like. Antiulcer agents such as, allantoin, aldioxa, alcloxa, N-methylscopolamine methylsuflate and the like. Antidiabetics such as insulin and the like.

For use with vaccines, one or more antigens, such as, whole-organism, natural, attenuated, heat-killed, chemically-inactivated, synthetic, peptides and even T cell epitopes peptides and the like. Some examples of the acronym of these antigens names include, but not limited to, GADE, DAGE, MAGE, etc.

The drugs mentioned above may be used in combination as required. Moreover, the above drugs may be used either in the free form or, if capable of forming salts, in the form of a salt with a suitable acid or base. If the drugs have a carboxyl group, their esters may be employed. Acids may be an organic acid, for example, methanesulfonic acid, lactic acid, tartaric acid, fumaric acid, maleic acid, acetic acid, or an inorganic acid, for example, hydrochloric acid, hydrobromic acid, phosphoric acid or sulfuric acid. The base may be an organic base, for example, ammonia, triethylamine, or an inorganic base, for example, sodium hydroxide or potassium hydroxide. The esters mentioned above may be alkyl esters, aryl esters, aralkyl esters and the like.

The present invention may be implanted into materials that include sutures, tubes, sheets, adhesion prevention devices, wound healing products, tissue healing agents and other tissue or cell growth promoters that further enhance the effectiveness of tissue regeneration. In addition, a voltage or current may be applied directly to the present invention at the repair, implant, transplant or reconstruction site. Polymers or other molecules with piezoelectric or electrically conducting properties may also be incorporated into the present invention. Several electroactive polymers exist including piezoelectric (e.g., polyvinylidene fluoride) and electrically conducting materials (e.g., polypyrrole (PP), and polythiophene). Since piezoelectric materials depend on small mechanical deformations to produce transient surface charges, the level and duration of focused stimulation cannot be controlled. In contrast, electrically conducting polymers readily permit external control over both the level and duration of stimulation. Thus strategies designed to enhance the regeneration of a responsive cell might employ electrically conducting polymers. For diagnostic purposes, the present invention may be incorporated not only with molecules containing active species but also with one or more detectable agents or molecules that allows for the diagnosis, monitoring, and/or prophylactic measures. Examples of suitable detectable agents include dyes, labels, metals, detection devices, and electronic chips.

The extended release microencapsulated active agents may be formed into compositions suitable for injectable use with the Vitelline protein B additive to encapsulate the active followed by dispersion in, e.g., sterile aqueous solutions and/or dispersions; formulations including sesame oil, peanut oil and/or aqueous propylene glycol; and/or sterile powders for the extemporaneous preparation of sterile injectable solutions and/or dispersions. In all cases the form must be sterile and/or must be fluid to the extent that easy syringability exists. It must be stable under the conditions of manufacture and/or storage and/or must be preserved against the contaminating action of microorganisms, such as bacteria and/or fungi.

Solutions of the active compounds as free base and/or pharmacologically acceptable salts may be prepared in water suitably mixed with a surfactant, such as hydroxypropylcellulose. Dispersions may also be prepared in glycerol, liquid polyethylene glycols, and/or mixtures thereof and/or in oils. Under ordinary conditions of storage and/or use, these preparations contain a preservative to prevent the growth of microorganisms.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle that contains the basic dispersion medium and/or the required other ingredients from those enumerated above. In the case of sterile powders for the preparation of sterile injectable solutions, the preferred methods of preparation are vacuum-drying and/or freeze-drying techniques that yield a powder of the active ingredient plus any additional desired ingredient from a previously sterile-filtered solution thereof. The preparation of more, and/or highly, concentrated solutions for direct injection is also contemplated, where the use of dimethyl sulfoxide (DMSO) as solvent is envisioned to result in extremely rapid penetration, delivering high concentrations of the active agents to a small tumor area.

Upon formulation, solutions will be administered in a manner compatible with the dosage formulation and/or in such amount as is therapeutically effective. The formulations are easily administered in a variety of dosage forms, such as the type of injectable solutions described above, but drug release capsules and/or the like may also be employed.

For parenteral administration in an aqueous solution, for example, the solution should be suitably buffered if necessary and/or the liquid diluent first rendered isotonic with sufficient saline and/or glucose. These particular aqueous solutions are especially suitable for intravenous, intramuscular, subcutaneous and/or intraperitoneal administration. In this connection, sterile aqueous media that may be employed will be known to those of skill in the art in light of the present disclosure. For example, one dosage could be dissolved in 1 ml of isotonic NaCl solution and/or either added to 1000 ml of hypodermoclysis fluid and/or injected at the proposed site of infusion, (see for example, "Remington's Pharmaceutical Sciences" 15th Edition, pages 1035-1038 and/or 1570-1580). Some variation in dosage will necessarily occur depending on the condition of the subject being treated. The person responsible for administration will, in any event, determine the appropriate dose for the individual subject.

In addition to the compounds formulated for parenteral administration, such as intravenous and/or intramuscular injection, other pharmaceutically acceptable forms include, e.g., tablets and/or other solids for oral administration; liposomal formulations; time release capsules; and/or any other form currently used, including cremes.

One may also use nasal solutions and/or sprays, aerosols and/or inhalants in the present invention. Nasal solutions are usually aqueous solutions designed to be administered to the nasal passages in drops and/or sprays. Nasal solutions are prepared so that they are similar in many respects to nasal secretions, so that normal ciliary action is maintained. Thus, the aqueous nasal solutions usually are isotonic and/or slightly buffered to maintain a pH of 5.5 to 6.5. In addition, antimicrobial preservatives, similar to those used in ophthalmic preparations, and/or appropriate drug stabilizers, if required, may be included in the formulation.

Additional formulations that are suitable for other modes of administration include vaginal suppositories and/or suppositories. A rectal suppository may also be used. Suppositories are solid dosage forms of various weights and/or shapes, usually medicated, for insertion into the rectum, vagina and/or the urethra. After insertion, suppositories soften, melt and/or dissolve in the cavity fluids. In general, for suppositories, traditional binders and/or carriers may include, for example, polyalkylene glycols and/or triglycerides; such suppositories may be formed from mixtures containing the active ingredient in the range of 0.5% to 10%, preferably 1%-2%.

Oral formulations include such normally employed excipients as, for example, pharmaceutical grades of mannitol, lactose, starch, magnesium stearate, sodium saccharine, cellulose, magnesium carbonate and/or the like. These compositions take the form of solutions, suspensions, tablets, pills, capsules, sustained release formulations and/or powders. In certain defined embodiments, oral pharmaceutical compositions will comprise an inert diluent and/or assimilable edible carrier, and/or they may be enclosed in hard and/or soft shell gelatin capsule, and/or they may be compressed into tablets, and/or they may be incorporated directly with the food of the diet. For oral therapeutic administration, the active compounds may be incorporated with excipients and/or used in the form of ingestible tablets, buccal tables, troches, capsules, elixirs, suspensions, syrups, wafers, and/or the like. Such compositions and/or preparations should contain at least 0.1% of active compound. The percentage of the compositions and/or preparations may, of course, be varied and/or may conveniently be between about 2 to about 75% of the weight of the unit, and/or preferably between 25-60%. The amount of active compounds in such therapeutically useful compositions is such that a suitable dosage will be obtained.

The tablets, troches, pills, capsules and/or the like may also contain the following: a binder, as gum tragacanth, acacia, cornstarch, and/or gelatin; excipients, such as dicalcium phosphate; a disintegrating agent, such as corn starch, potato starch, alginic acid and/or the like; a lubricant, such as magnesium stearate; and/or a sweetening agent, such as sucrose, lactose and/or saccharin may be added and/or a flavoring agent, such as peppermint, oil of wintergreen, and/or cherry flavoring. When the dosage unit form is a capsule, it may contain, in addition to materials of the above type, a liquid carrier. Various other materials may be present as coatings and/or to otherwise modify the physical form of the dosage unit. For instance, tablets, pills, and/or capsules may be coated with shellac, sugar and/or both. A syrup of elixir may contain the active compounds sucrose as a sweetening agent methyl and/or propylparabens as preservatives, a dye and/or flavoring, such as cherry and/or orange flavor.

The mixed release pharmaceutical formulations disclosed herein may be administered, e.g., parenterally, intraperitoneally, intraspinally, intravenously, intramuscularly, intravaginally, subcutaneously, or intracerebrally. Dispersions may be prepared in glycerol, liquid polyethylene glycols, and mixtures thereof and in oils. Under ordinary conditions of storage and use, these preparations may contain a preservative to prevent the growth of microorganisms. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal and the like. In many cases, it will be preferable to include isotonic agents, for example, sugars, sodium chloride, or polyalcohols such as mannitol and sorbitol, in the composition. Prolonged absorption of the injectable compositions may be brought about by including in the composition an agent that delays absorption, for example, aluminum monostearate or gelatin.

Sterile injectable solutions may be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile carrier that contains a basic dispersion medium and the required other ingredients from those enumerated above. In the case of sterile powders for the preparation of sterile injectable solutions, the methods of preparation may include vacuum drying, spray drying, spray freezing and freeze-drying that yields a powder of the active ingredient (i.e., the therapeutic compound) plus any additional desired ingredient from a previously sterile-filtered solution thereof.

The bioactive may be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the therapeutic compound may be incorporated with excipients and used in the form of ingestible tablets, buccal tablets, troches, capsules, elixirs, suspensions, syrups, wafers and the like. The percentage of the therapeutic compound in the compositions and preparations may, of course, be varied as will be known to the skilled artisan. The amount of the therapeutic compound in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical carrier. The specification for the dosage unit forms of the invention are dictated by and directly dependent on (i) the unique characteristics of the therapeutic compound and the particular therapeutic effect to be achieved; and/or (ii) the limitations inherent in the art of compounding such a therapeutic compound for the treatment of a selected condition in a subject.

Vitteline protein B (vpB) is one of three proteins used by parasitic worms to produce an encapsulant to protect the developing embryo. The protein eggshell is formed predominantly of vpB through the use of protein precursors which become crosslinked during the maturation process through the use of dihydroxphenylalanine residues. VpA and vpC, found in small quantities in the eggshell, are believed to be involved in deposition and spreading of vpB. As an immature, uncured protein, vpB demonstrates adhesive properties; as a fully cured protein it serves as a novel sealant which is resistant to acids, bases, heat, light, dessication, and proteolysis. In addition the shell material is biocompatible and non-antigenic. It has been found that vpB's resistance to proteolysis makes it an ideal additive for microcapsules and micro- and nanoparticles, extending particle life when introduced into an animal. The vpB protein may also be used as a protein adhesive in aqueous environments.

Vitelline protein B is a member of a family of proteins with variable sequences, however, the amino acid composition is fixed. The present inventors cloned and sequenced two members of the vpB gene family and find their amino acid sequence to vary only within the central 33% of the gene sequence.

As shown in FIG. 1, the sequence varies, the amino acid composition of the two vpBs (vpB1 and vpB2) is very similar; furthermore their amino acid composition is nearly identical to that of the eggshell itself. As shown here the amino terminal (N) ends of the proteins (approximately ⅓) and the carboxy terminal (C) ends of the proteins (⅓) are identical when comparing the two amino acid sequences. However the central one third of the two proteins diverge significantly at the amino acid level (35%). This shuffling of amino acids still preserves the amino acid composition and the functionality of these materials.

Table 1 summarizes the conservation of the amino acid composition of two VpB proteins.

| AMINO ACID | Purified vpB PROTEIN | VpB1 cDNA* | VpB2 cDNA* |
|---|---|---|---|
| ASX | 140 + 4.3 | 158.1 | 134.0 |
| THR | 18 + 3.1 | 15.8 | 15.8 |
| SER | 52 + 4.8 | 55.3 | 51.4 |
| GLX | 83 + 3.7 | 83.0 | 75.1 |
| PRO | 16 + 0.9 | 11.9 | 11.9 |
| GLY | 165 + 4.6 | 150.2 | 154.2 |
| ALA | 69 + 2.4 | 71.1 | 71.1 |
| CYS/2 | 0 | 0 | 0 |
| VAL | 9 + 2.1 | 7.9 | 4.0 |
| MET | 23 + 4.2 | 23.7 | 23.7 |
| ILE | 5 + 1.0 | 4.0 | 0 |
| LEU | 38 + 1.4 | 35.6 | 35.6 |
| DOPA | 106 + 9.8 | | |
| TYR | 21 + 5.0 | 134.4 | 138.3 |
| PHE | 38 + 3.1 | 35.6 | 35.6 |
| HIS | 45 + 3.7 | 33.3 | 55.3 |
| LYS | 120 + 6.5 | 114.6 | 126.5 |
| ARG | 60 + 3.2 | 63.2 | 67.2 |
| TRP | 0 | 0 | 0 |

*values represent mature vpB exclusive of signal sequence.

As such, the composition rather than the sequence of these proteins is responsible for the properties of 1) resistance to proteolysis and 2) adhesiveness.

Polymers containing catecholic groups are widespread in nature and perform diverse functions. In microbial systems the polymers consist of short peptides whose function is to sequester ferric iron from the environment (Raymond and Carrano 1979, Ong et al 1979). In marine invertebrates such as mussels and tunicates the catecholic polymers are proteins modified by the presence of dihydroxyphenylalanine (DOPA) residues whose function is underwater sealant and adhesive (Waite et al 1985, Waite 1986). The synthetic counterparts of these polymers have found widespread application in industry as semiconductors (Jaegfeldt et al 1983, Lau and Miller 1983), metal chelators (Pecoraro et al 1981), electrocatalysts (Degrand 1985) and adhesives (Pizzi 1985) to name a few. Additional interest in DOPA compounds has been generated by the recent finding that DOPA derivatives may act as redox cofactors at the active site in amine oxidases (Janes et al 1990). The freshwater trematode, *Fasciola hepatica*, produces a catecholic protein polymer which functions as a structural protein in egg microencapsulation. The polymer is cross-linked and quinone-tanned to produce a sclerotized egg case with extraordinary properties.

*Faciola hepatica* is a digenetic trematode which encapsulates its eggs in a proteinaceous shell. The shells are a prototypical microencapsulating system that protects *Fasciola* eggs from the host natural defenses while allowing uptake of essential nutrients and release of metabolic products. The long-term stability of this natural composite material results from crosslinks formed by quinone tanning or sclerotization of specialized eggshell proteins in which tyrosine residues have been post-translationally modified to 3,4-dihydroxyphenylalanine (DOPA). The present inventors purified and characterized the three major protein components of the shell, vitelline proteins A, B and C (vpA, vpB, and vpC). In addition, cDNAs encoding two variants of the major eggshell component have been sequenced and expressed as recombinant protein. The proteins encoded consist of highly degenerate repeats of a hexapeptide enriched in glycine and containing clusters of basic amino acid residues as well as clusters of acidic residues.

The vitelline proteins, natural encapsulating agents, offer several advantages over materials in current use, such as synthetic polymers and gelatin. (1) As recombinant proteins they can be obtained in bulk with uniform and defined characteristics. (2) The protein compositions can be genetically engineered to vary the density of tyrosine/DOPA residues, or introduce cysteine residues and so control the cross-linking characteristics and the resultant porosity and stability of microcapsules. (3) The cross-linking agent is already integrated into the protein and need be only oxidized, either spontaneously or with easily separable reagents, to initiate curing. (4) the vitelline proteins are poorly antigenic. (5) Though durable, cured protein is (ultimately) biodegradable and non-toxic.

Synthetic microencapsulation. Proteins have enjoyed extensive use as encapsulating agents and so there exist numerous protocols which may be applied to vitelline protein microencapsulation. In essence, all approaches involve the induction of a phase separation in a mixture of core material and encapsulating agent such that the core is efficiently engulfed by the encapsulating agent, usually followed by stabilization of the microcapsule walls by low molecular weight cross-linking agents such as glutaraldehyde. Phase separations are commonly induced by i) manipulation of temperature, pH, salt or alcohol concentrations; ii) addition of incompatible polymers; iii) liquid coacervate formation; and iv) congealing or denaturation in oil emulsions. Others approaches are suggested by the biochemical properties of vpB, such as interfacial polymerization at liquid/liquid interfaces or the stabilization of liposomes encased in vitelline protein by covalent cross-linking.

The present inventors have studied the mechanism by which the worm microencapsulates in order to mimic that process in vitro. The worm carries out the process of microencapsulation by applying a film of eggshell precursor protein to the surface of a lipoprotein layer or interface formed in the lumen of Mehlis' gland, the site of eggshell assembly. A catechol oxidase activity oxidizes the DOPA residues of the eggshell precursor to DOPAquinone. The highly reactive DOPAquinone is postulated to spontaneously form a number of types of chemical cross-links although in this system lysine or histidine appear to be the primary nucleophiles participating in cross-linking. Faithfully mimicking the worm's approach will therefore involve the use of liposome encapsulation followed by spreading of recombinant eggshell protein on the outer surface of the liposome. A commercially available mushroom tyrosinase may then be employed to crosslink the shell precursor proteins in vitro and to cure the microcapsule.

Alternatively, coacervation methods based on gelatin microcapsulation (simple coacervation) or gelatin/acacia microencapsulation (complex coacervation) may be used. Either approach eliminates the need to first encapsulate the core material in a liposome prior to encapsulation with vitelline protein.

One or more of vitelline proteins vpA, vpB, and vpC may be contacted with an agent to be microencapsulated under conditions suitable for microencapsulation. The agent can be a peptide, protein, nucleic acid, pharmaceutical, or other organic chemical compound. The nucleic acid and protein sequence of vpB can be found at the NCBI database, Accession No. M93024. Additionally, the vitelline proteins may be modified by enzymatic or chemical post-translational modification. One example of such a modification is the hydroxylation of one or more tyrosine residues. Additionally, fragments of the vitelline proteins can be used in place of, or in combination with the full length naturally occurring proteins.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the scope of the invention.

EXAMPLES

Example 1

Purification and Characterization of Protein Components of Shells

Documentation of *Fasciola hepatica* eggshell production has historically included a quinone tanning process which involves cross-linking of proteins containing catecholic groups (Smyth and Clegg, 1959). However the nature of the substrates involved in the cross-link and the structure of the cross-link itself have been subjects for heated debate and novel investigative approaches. Waite and Rice-Ficht demonstrated the abundance of dihydroxyphenylalanine (DOPA) in the shell producing glands of the worm (vitellaria) as well as in the shells themselves using a DOPA specific reagent recognizing only monosubstituted 1,2 benzenediols and producing a bright red chromophore. The results were highly suggestive that DOPA is at least one of the major substrates for oxidation and protein crosslinking. Several DOPA-containing protein precursors of the shell were subsequently purified and characterized. The three major DOPA-containing proteins of the worm are rich in glycine and DOPA and compose three major size classes of 70 kDa, 31 kDa and 17 kDa. Each protein also has a distinctive amino acid composition with the 70 kDa protein rich in ASX and ARG, the 31 kDa protein rich in LYS and ASX the 17 kDa protein rich in HIS.

Example 2

Characterization of 31 kDa vpB Protein

The 31 kDa protein (vitelline protein B, vpB) has been purified and characterized in detail (Waite and Rice-Ficht 1987; Waite and Rice-Ficht 1992, appendix 3; and Rice-Ficht and Waite 1992, appendix 2). Sequence analysis of tryptic peptides derived from this protein constituted the first direct demonstration that DOPA residues were in fact a component of the peptide backbone and were likely formed through post-translational modification of tyrosine residues of the precursor protein; this parallels observations in the adhesive proteins of the marine mussel, Mytilis edulis, (Waite and Tanzer 1980) but is quite distinct from other mechanisms documented for quinone tanning such as that employed by insects in the formation of cuticles and egg cases (Richards 1978). The protein has an apparent molecular weight of 31,000, a pI of 7.4 and constitutes approximately 7% of the protein in adult *Fasciola hepatica*. Eleven percent of the amino acid residues of the protein are DOPA residues which 'disappear' during shell curing in vivo or during treatment with mushroom polyphenol oxidase in vitro.

Example 3

Isolation of cDNA Encoding vpB Protein

Isolation of cDNAs encoding the 31 kDa protein was achieved using a combination of antibody selection and hybridization with degenerate oligonucleotides (Rice-Ficht and Waite 1992). The proteins encoded are approximately 30,900 daltons and bear a striking homology with the amino acid composition of the purified protein. Sequencing of cDNAs has revealed the presence of at least two distinct mRNAs encoding vitelline protein B1 (vpB1) and vitelline protein B2 (vpB2) which are markedly different in amino acid sequence (33% variation) but quite similar in amino acid compositions. Southern blot analysis also indicates the presence of at least six gene copies for the 31 kDA protein when vpB1 is employed as a hybridization probe under stringent conditions. These results led to a re-examination of the apparently homogeneous 31 kDa protein and revealed microheterogeneity and the presence of a family of proteins.

The electrophoretic microheterogeneity is attributed to i) varying degrees of post-translational modification (TYR to DOPA) and ii) the presence of mRNAs varying in primary sequence (Waite and Rice-Ficht 1992, appendix 3). Fractionation of the purified protein was achieved through C-8 reversed phase HPLC; and the fractions across the vpB peak were subjected to amino acid analysis. All amino acids were constant across the peak with the exception of tyrosine and DOPA. DOPA residues were high on the leading edge of the peak and declined with increasing acetonitrile concentration; the converse was true of tyrosine residues suggesting a precursor-product relationship. N-terminal sequence analysis of protein fractions across the peak indicates that all proteins share the same N-terminus. This data taken alone might indicate that the heterogeneity was due solely to post-translational modification. However, extensive sequencing of tryptic peptides has shown the presence of peptides unique to the vpB1 mRNA and to the vpB2 mRNA.

Both vpB1 and vpB2 contain the N-terminal peptide sequence defined through vpB peptide analysis. Southern hybridization was carried out on duplicate filters using either the vpB1 gene as probe or an oligonucleotide which represents the N-terminus of all vpB proteins (data not shown). There appear to be 6-7 structural genes for this family of proteins while the N-terminal sequence is associated with only one copy. However, the data derived from sequencing vpB1 and vpB2 indicates that at least two different transcripts carry this N-terminal sequence. The possibilities for this dichotomy are many but the likeliest explanations are cis, trans or possibly differential RNA splicing are placing the single N-terminal coding sequence on multiple transcripts; this is being pursued. One approach to studying the number of transcripts which bear the N-terminal sequence is to employ PCR using RNA as substrate.

Example 4

Characterization of 17 kDa vpC Protein

Analysis of the 17 kDa eggshell protein (vitelline protein C, vpC) has revealed a similar heterogeneity with the presence of at least four distinct electrophoretic types. Apparent molecular weights range from 16,000 to 18,500 while pIs under denaturing conditions indicate the presence of only two species of 6.89 and 6.99. A single amino terminal peptide sequence is detectable and has been employed as a tool for gene isolation using degenerate oligomers. The amino acid composition of vpC is remarkable in that DOPA (20%), histidine (20%), and glycine (41-42%) comprise 80% of the amino acid residues in all variants of the family. The bulk of the molecule is composed of a (GLY-X)n repeat motif in which X is SER, DOPA or HIS. The only feature which this protein shares with the 31 kDa protein is the presence of DOPA residues. The four or more variants observed in the vpC family do not arise as a result allelic differences between individuals since a survey of six morphologically different worms indicates the presence of all vpC variants in each individual (Waite and Rice-Ficht 1989).

Example 5

Temporal and Spatial Expression of RNA and Proteins

Through the use of antisera specific for the 31 kDa protein and through in situ hybridization it has been possible to study the localization of expression of the major DOPA protein. The use of a rabbit antisera raised against the purified vpB in tissue localization studies has indicated a high level of the protein within vitelline cells localized to the vitelline glands at the worm periphery (Rice-Ficht 1992); reactivity of antisera corresponds to the vitelline globules of mature vitelline cells (Rice-Ficht and Waite, 1992; appendix 2) and is evident before vitelline cells pass into the vitelline reservoir for delivery to Mehlis' gland, the site of shell assembly. The 31 kDa protein is synthesized and stored in vitelline granules of vitelline cells still residing in the vitelline gland follicle.

In situ hybridization using the carboxyterminal 40% of the vpB1 gene agrees with the antibody localization data (Rice-Ficht and Waite 1992). Transcripts encoding vpB1 are most abundant in the earliest form of mature vitelline cell residing in the vitelline gland. The protein apparently enters a pathway for regulated secretion and is stockpiled in globules of the vitelline cell cytoplasm. A putative chemical signal elaborated by Mehlis' gland triggers release of the globules and the initiation of capsule assembly.

Example 6

Putative Models for Shell Assembly

Based on a body of histological and histochemical data reviewed by Smyth and Clegg (1959), metabolic labeling studies (reviewed by Rice-Ficht 1992) and the current biochemical analysis of eggshell proteins, a biological and biochemical model of shell assembly are proposed. In these models all three shell precursor proteins are translated in the extensive GER of the early vitelline cells and stockpiled in globules prior to the time that the cells leave the follicle. Nascent protein precursors are modified by a putative protein-specific tyrosyl hydroxylase to produce Dopa residues in the protein backbone. The polyphenolic shell precursors (Smyth 1954; Waite and Rice-Ficht 1989) and polyphenol oxidase (Smyth 1954) are transported to the ootype and packed away in vitelline cell globules. As vitelline cells congregate in the ootype along with one fertilized ovum, Mehlis' gland forms a lipoprotein membrane (Clegg 1965) around the vitelline cell/egg mass which is followed by release of globular material from the vitelline cells through regulated secretion. As the globule contents spread on the lipoprotein membrane, catechol oxidase becomes activated and oxidation and crosslinking ensues. Dopa residues are abundant in newly formed shells and shells of the proximal uterus. As the shells pass through the uterus, Dopa residues are consumed in the crosslinking reactions (as ascertained through DOPA-specific staining; Waite and Rice-Ficht 1989) and the shells are completely 'cured' prior to extrusion.

Some clues to the role of individual proteins in shell formation have presented themselves. VpB is the major shell component by weight and is present in molar quantities approximately 30 times that of vpA or vpC. Of the three proteins studied only one, VpC, has substantial homology with any published protein sequence; vpC shows strong homology with the his-rich domain of high molecular weight kininogen I whose function is to bind to negatively charged surfaces and accelerate binding of other blood clotting factors to that surface (Kitamura et al 1983). Based on this homology, it is postulated that vpC is the first of the shell proteins to associate with the lipoprotein layer, facilitating binding and dispersion of vpB and vpA during shell formation.

Example 6

Characterization of the 70 kDa DOPA Containing Protein of the Eggshell

The 70 kDa protein (vitelline protein A, vpA) is the last of the three major DOPA containing protein precursors of the eggshell remaining to be characterized. Preliminary amino acid analysis has indicated a high ASN/ASP (21%), GLY (11%) and ARG (8%) content with 4% DOPA residues and a substantial amount of unmodified tyrosine. One of the future goals of the project is to compare in vitro modification of the vpA, vpB and vpC with various polyphenol oxidases in order to probe the factors governing modification of individual tyrosine residues. Further characterization will include analysis for microheterogeneity and limited peptide sequencing.

Example 7

Purification and Characterization of the *F. hepatica* Catechol Oxidase

Present evidence suggests that catecholoxidase activity is present in mature vitelline cells as well as eggshells of *F. gigantica* (Nellaiappan & Ramalingam, 1980), *S. mansoni* (Seed and Bennett 1980), *S. japonicum* (Wang et al 1986), and *Parapleurus sauridae* (Nellaiappan and Ramalingam 1980), where it presumably catalyzes the oxidation and subsequent polymerization of the eggshell precursor proteins to a quinone-tanned material. These studies, however, do little more than confirm the presence of enzyme activity.

*F. hepatica* from freshly condemned bovine livers will be obtained from the slaughterhouse in Sealy, Tex. and transported to the laboratory on dry ice. Extraction of soluble enzyme activity from the vitellaria is complicated by at least three factors, a) vitellaria interdigitate with the digestive diverticulum hence any extraction is likely to contain enzyme with some contaminating proteases, b) like zymogens, the catecholoxidases of insects, frog skin and mussels (Waite 1985) are stockpiled in latent form prior to secretion, and c) the catecholoxidases implicated in quinone-tanning reportedly have odd solubility requirements and commonly become co-crosslinked to their substrates.

In order to address these concerns, enzyme extractions will be done using buffers with a broad spectrum of protease inhibitors, e.g., 1 M phenylmethylsulfonylfluoride, 10 mM N-ethylmaleimide, 25 mM ethylenediaminetetraacetic acid (EDTA). Good activation of other latent catecholoxidases has been achieved with trypsin and, especially, chymotrypsin treatment. There is no fait accompli recipe for solubilizing catecholoxidase activity from vitelline cells. Wang, et al., (1986) extracted the enzyme from S. japonicum with unbuffered 0.25 mM sucrose, others have utilized unbuffered 0.25 M sucrose (Nellaiappan and Ramalingam, 1980) and 0.01 M sodium phosphate at pH 7.2 (Thangaraj et al 1986) to solubilize enzyme from monogeneans. Unfortunately, Seed et al., (1978) and Mansour (1958) report a conflicting conclusion that catecholoxidase activity in F. hepatica and S. mansoni is not soluble in 0.1 M potassium phosphate at pH 6.8. Clearly, many of these studies are of marginal value and should be redone. Some precautions to improve yields might be to use 1 M NaCl in the extraction buffer. This improves recovery of enzyme from quinone-tanned byssal threads (Waite 1986). Addition of potassium cyanide or salicylaldoxime to crude extracts may reduce premature oxidations by the enzyme, and use of borate as the extraction buffer will complex (hence inactivate) intrinsic substrates such as DOPA-containing proteins.

Example 8

Purification of Extracted Enzyme

Purification of the extracted enzyme will be attempted by ion exchange chromatography and gel filtration. The assay of catecholoxidase activity will be done using the assay based on the formation of quinone-proline adducts (Rzepecki and Waite 1989) and by measurement of $O_2$ consumption using an oxygen electrode (Duckworth & Coleman 1970). The formation of quinone-proline adducts is linear with time and results in a deep purple chromophore (molar $E_{390}$=8300 $cm^{-1}$). Following the purification of the enzyme, a physical characterization of the enzyme will include molecular weight determination by gel filtration using the appropriate range of standards, subunit molecular weight determination by SDS PAGE, and prosthetic metal determination by atomic absorption spectroscopy. All polyphenoloxidases known to date are copper proteins. Amino acid composition will be performed following protein hydrolysis according to Tsugita, et al, (1987). The N-terminus of purified subunits will be sequenced by Edman gas phase methodology (Ozols 1986). An alternate approach will be an enzyme isolation from newly formed eggshells, purified from the Fasciola uterus; complete digestion of the shells with highly purified enzymes specific for DOPA residues (from the marine organism Alteromonas, see below in cross-link analysis) may release the catecholoxidase. Since the enzyme is known to be active even in completely cured eggshells this approach may yield some positive results.

Enzyme-substrate kinetics will be a particular focus of these studies. A comparison of the Michaelis-Menten behavior of the vitelline and eggshell enzyme activities with various synthetic mono- and diphenols and $O_2$ will be performed. In addition, DOPA-containing peptides derived from protease digests of vitelline proteins B and C will be employed as substrate. Effect of inhibitors, pH, and temperature will be determined using the best substrate (highest Vmax/Km) and heat denatured-controls. Use of intact proteins as substrates is impractical due to the insolubility of these without borate at physiological pH (Waite and Rice-Ficht 1987).

In structures undergoing quinone tanning such as nascent eggshells, it is not clear whether assembly occurs in a liquid crystal or solid-state (Bouligand, 1985; Waite, 1985). The amount of enzyme present would certainly have a bearing on which of the states existed. In the liquid crystal, the enzyme would presumably have more freedom to move from one crystalline precursor to another in the course of introducing crosslinks. In the solid state, in contrast, enzyme activity would be severely localized e.g., as in an eggbox and much more of it would be required relative to the liquid crystal model to effect crosslinking. Information about the concentration of enzyme in the eggshells could thus indirectly at least invalidate the liquid crystal or solid state models. If the specific activity of catecholoxidase purified from vitelline cells can be calculated, then in principle, the total amount of active enzyme per mg eggshell protein can be estimated according to Segel (1976). Recall that catecholoxidase activity persists in eggshells even after release of the egg from the host (Smyth and Clegg 1959). The major assumption will be that the specific activity of the enzyme is not drastically altered once it becomes part of the eggshell. Total protein in the eggshell will be quantitated by amino acid analysis following hydrolysis. A corroborative estimate of the amount of catecholoxidase in eggshells (based on the mol % Cu detected in purified catecholoxidase) could be attempted by doing atomic absorption measurements on hydrolyzed eggshells. Here the assumption would be that all eggshell Cu is from the catecholoxidase.

Numerous attempts to purify the trematode catechol oxidase from freshly prepared worms applying techniques successfully employed in M. edulis have been unsuccessful. Techniques which successfully fractionate the enzyme often lead to its inactivation before homogeneity can be achieved. A new purification scheme involving the use of phase partition with Triton X 114 (Bordier 1981; Sanchez-Ferrer 1989) will next be employed to fractionate and purify the trematode enzyme. The enzyme plays a pivotal role in eggshell assembly and its purification is a priority of the project. Initial characterization of the trematode enzyme in relatively crude preparations indicates it to be present in stoichiometric rather than enzymatic quantities with respect to the shell precursor proteins vpA, vpB and vpC. This raises the distinct possibility that the enzyme is not only catalytic but an integral part of the shell architecture becoming crosslinked and immobilized during shell assembly. This possibility is underscored by the fact that the enzyme may be assayed in partially cured eggshells but never isolated (data not shown). Histochemical evidence also suggests that the enzyme is present in an inactive form even in newly formed vitelline globules as an emulsion with the vpA, vpB and vpC substrates. This provides the enzyme/substrate combination in a premixed form prior to spreading and quinone tanning.

An alternate approach to enzyme purification by conventional methods will be an affinity purification scheme; this approach would utilize antibody directed against recombinant catechol oxidase coupled to cyanogen bromide activated sepharose beads. This approach is dependent upon isolating the gene first and producing recombinant protein from that gene (objective IIIB) Affinity purification using substrate covalently attached to beads (i.e. a methyl catechol) might also be employed by a method analogous to that used for the purification of the *Schistosoma* glutathione-S-transferase via bead-bound glutathione (Smith and Johnson 1988).

Example 9

Characterization of cDNAs Encoding the 17 kDa Proteins cDNAs were isolated from lambda gt10 and lambda gt11 *F. hepatica* libraries using hybridization and a degenerate oligonucleotide probe. The N-terminal sequence of vpC was employed to produce a 29-mer using inosine substitution at the most degenerate positions in order to limit the number of oligonucleotides in the mix (Ohtsuka et al 1985). The probe was employed using tetramethylammonium chloride salts, a method which provides a base composition-independent hybridization (Wood et al 1985). The hybridization can be controlled as a function of probe length only, enhancing results when screening a complex library with a pool of oligonucleotide probes. A number of cDNAs of 500-600 base pairs in length have been isolated and sequence is being determined Sequencing is proceeding through application of asymmetric polymerase chain reaction (Gyllensten and Erlich 1988) directly from the selected lambda library clones. Primers flanking cDNA insertion sites in the vector are employed to amplify the DNA; following a brief extraction procedure to remove primers and nucleoside triphosphates the PCR product is subjected to sequencing with standard dideoxy chain termination methods and T7 polymerase (Sanger and Coulson 1975). This method which circumvents subcloning and other low-efficiency, time consuming procedures is being employed to examine the clones.

Example 10

Isolation and Characterization of cDNAs Encoding the 70 kDa DOPA Protein

A similar approach may be used to isolate the vpB1 and vpB2 genes (Rice-Ficht and Waite 1992). Adult *F. hepatica* libraries have been constructed in this laboratory and include cDNA libraries in lambda gt10 and lambda gt11 and genomic libraries in lambda 2001 and lambda DASH; each has been used successfully for gene isolation. In view of the low level antigenicity of vpB and vpC a dual approach to gene isolation will be continued. Antibody will be raised to the purified vpA and employed for cDNA isolation from the lambda gt11 library (Davis and Young 1983). Limited peptide sequencing will also be employed to define oligonucleotides for library screening and gene isolation. (Wood et al 1985).

Example 11

Isolation of the Gene Encoding Trematode Catechol Oxidase

Lambda gt11 libraries produce proteins as a fusion with the 116 kDa b-galactosidase gene which may easily interfere with proper folding and activity of the cloned enzyme. Early attempts to carry out plaque assays with Arnow's reagent (Arnow 1937) and 4-methyl catechol were unsuccessful due to the solubility and instability of the chromophore produced. A modification of this protocol (Rzepecki and Waite 1989) producing a more intense color reaction was also employed without success. An alternate approach using an antibody (polyclonal) directed against the Mytilis edulis catechol oxidase will be used to identify cloned trematode enzyme in an expression library. Although catechol oxidases investigated to date from various sources due not share significant nucleotide or amino acid sequence homology, secondary structures of the enzymes may be similar. Additionally, the trematode and mussel enzymes may be more closely related in structure in view of the similarities in substrates (protein-bound tyrosine) and processes in which they participate.

Example 12

Selection of cDNAs Encoding Proteins Specific to Mehlis' Gland from a Mehlis' Gland Specific Expression Library The Mehlis' gland constitutes the biochemical "black box" of eggshell formation; among the functions attributed to the gland are i) initial entrapment of 30 vitelline cells and one ovum in a lipid bilayer (Wharton 1983), ii) signaling the release of vitelline globules from the vitelline cells and iii) activation of the catechol oxidase enzyme. In an effort to identify additional products and processes involved with shell manufacture and the production of the shell material, a selection process will be carried out to identify proteins manufactured only in Mehlis' gland. One interesting observation in our laboratory involves the finding that histochemically the uterine lining which interfaces with Mehlis' gland contains a high concentration of membrane-bound alkaline phosphatase. This is only one example of Mehlis' gland specific products which may be isolated via the process outlined here. We postulate that the presence of this enzyme may be significant in relation to production of a phosphate buffering system in the lumen of Mehlis' gland. pH may be especially important in the spreading properties of histidine rich proteins (i.e. vpC) since the imidazole pK is near pH 7.0 (Rice-Ficht 1992).

The production of a Mehlis' gland-specific cDNA library will be carried out through the standard techniques first applied to the manufacture of T cell-specific cDNA libraries via "subtraction hybridization" (Hedrick et al 1984). For this procedure flash frozen worms will be partially thawed and the Mehlis' gland area from 50 worms excised and pooled; the anterior portion or "head" of the worms will also be pooled. The anterior portions are assumed to contain the standard housekeeping genes found in all cell types and will be used to remove unwanted RNA from the Mehlis' gland preparation prior to cDNA synthesis. RNA will be extracted from the tissues as described (Rice-Ficht and Waite 1992) and a first strand cDNA synthesized using the Mehlis' gland RNA as template. The cDNA will be hybridized to a 100-fold excess of head RNA and applied to hydroxyapatite. The cDNA not retained by the column should be single-stranded and unique to Mehlis' gland; a second cDNA strand will be synthesized and the cDNA introduced into lambda gt11 and lambda gt10 for amplification. There are alternate protocols to achieve the same objective including deletion enrichment (Lamar and Palmer 1984) and a plus/minus screening for standard cDNA libraries (Tedder et al 1988; Zurita et al 1987).

cDNAs of interest will be located using antibody prepared against excised Mehlis' gland or through a plus/minus hybridization technique (Tedder et al 1988). The later relies on screening duplicate plaque lifts from a cDNA library with a radiolabeled cDNA representing first the tissue of interest (i.e. Mehlis' gland) and secondly a tissue containing background genes (i.e. the worm 'head'). Plaques screening positive with the gland probe and negative with the head probe would be candidates for further study. The Mehlis' gland specific nature of candidate sequences will be determined through i) in situ hybridization of the cloned segment to worm sections to verify its presence in Mehlis' gland, ii) production of recombinant protein against which polyclonal and monoclonal antibody would be raised for tissue localization studies or iii) sequencing of the cDNA through polymerase chain reaction to perform a preliminary search of the gene bank.

A limited success with the production of monoclonal antibody against the shell precursor proteins prompted a multifaceted approach to gene isolation. Additionally, monoclonal antibody is often a poor reagent for clone selection from expression libraries due to the fact that only a single epitope is recognized by the antibody. The major utility of monoclonal antibody will be in tissue localization of proteins and fine structure mapping at the EM level.

Example 13

Analysis of the Metal Composition of Shells Isolated Directly from the Trematode Uterus The suggestion has been made that various metals are associated with trematode vitellaria. The observation of "calcareous corpuscles" within the mature vitelline cells of *Schistosoma mansoni* which are rich not only in calcium but in phosphorus and magnesium as well (Shaw and Erasmus 1984) is one of the strongest. Coupled with the fact that DOPA residues have extraordinary binding constants for a number of metals we propose to examine the metal content of the vitelline cells of *F. hepatica* as well as purified eggshells for metal composition. Initial studies will be carried out using electron probe microanalysis and energy dispersive X-ray spectroscopy (Shaw and Erasmus 1984). Element quantities as small as 10-18 g in subcellular structures may be probed (Hall 1979). Cryosections of adult worms will be employed to minimize changes which might occur with fixation. Both vitelline cells and eggshells within the worm will be examined in cryosection although additional analysis of shells carefully purified from contents in the absence of metal chelating agents will be performed. The electron probe microanalysis technique is preferred initially over more precise physical methods because it requires less material and should serve well for initial survey purposes.

Example 14

Study of Metabolism and Deposition of Shell Protein Components

Tissue culture techniques in trematodes have been largely unsuccessful in the study of eggshell formation. Although many aspects of worm metabolism are apparently preserved under standard culture conditions shell deposition becomes markedly aberrant after only minutes to hours in culture (Clegg 1965; Smyth and Clegg 1959); free vitelline cells and free globules of shell precursor material rapidly appear in the proximal uterus during culture, a phenomenon which is not observed in worms immediately after removal from the host. Although egglaying by trematodes continues for hours to days after introduction into culture, the process relies on preformed RNA and protein since RNA production for shell precursor ceases with introduction to culture (Reis et al 1989). The present inventors conducted culture of trematodes in fertilized chicken eggs as recently reported by Fried (1989) for other genuses of flatworm and found that egglaying proceeds in an apparently normal fashion (i.e. a lack of vitelline cells or free vitelline globules in the uterus) for extended periods of time (tested up to ten days). Analysis of culture worms for the presence of mRNA complementary to shell precursor protein genes is underway. Since *F. hepatica* is auxotrophic for a remarkable number of compounds including purines, pyrimidines, sterols, fatty acids, and a number of amino acids (Kurelec 1972) we anticipate the ability to successfully label macromolecules even in amniotic fluid of the avian egg. Successful isotopic labeling of shell precursor proteins will enable a range of analyses concerning shell crosslinking and shell architecture to be performed.

Example 15

Analysis of Eggshell Cross-Links Using Solid State Nuclear Magnetic Resonance NMR Cross-links in insect cuticle have been successfully probed employing solid state $^{13}$C and $^{15}$N NMR (Schaeffer, et al, 1987). In this procedure tobacco hornworm larvae were injected with either 13C (ring labeled) dopamine to label catechols or with $^{15}$N histidine; NMR analysis of intact cuticle revealed the presence of covalent linkages between protein bound histidine and catecholamine dopamine. Similar analyses will be carried out in the trematode system labeling worms with $^{13}$C tyrosine as DOPA precursor, $^{15}$N lysine and $^{15}$N histidine to probe possible crosslinks between vpB, rich in DOPA and lysine, and vpC, rich in DOPA and histidine.

Example 16

Analysis of Eggshell Cross-Links Using Proteolysis with Dopa Specific Enzymes

Another approach to characterize crosslinks would rely on the use of Dopa-protein digesting proteases recently described from the marine *Alteromonas* species (Dohmoto and Miyachi 1991). These enzymes completely digested byssyl thread and were found to contain at least two proteases that preferentially cleaved the peptide bond next to DOPA. For this study we propose to digest eggshells harvested and cleaned from the uteri of *F. hepatica* with a crude *Alteromonas* protease (buffer 0.1M Tris-ascorbate pH 7.5) for as long as necessary to render the eggshells completely soluble. When this has been accomplished, residual material will be removed by centrifugation, and the supernatant lyophilized, redissolved in 5% acetic acid and separated on C-18 reversed phase HPLC. Fractions containing aromatics will be examined by amino acid analysis, UV spectrophotometry and, if encouraging, by mass spectrometry.

Example 17

Analysis of Eggshell Cross-Links Using Specific Labeling Through Nucleophilic Addition of $^{14}$C Glycine Ethylester The greatest limitation in working with quinone-tanned proteins is that they typically resist every treatment short of complete hydrolysis. For this reason entirely, it is expedient to work with pretanned precursors. The present inventors adopted a labeling protocol developed by Simon and Green (1988) for following the course of cross-linking in involucrin, a major protein of the epidermis. Like the vpB and vpC, involucrin (mol. wt. 100 kDa) consists of a degenerate series of repeating consensus decapeptides that are rich in glutamine (Eckert and Green 1986). It was recently observed that involucrin in terminally differentiated epidermal cells is associated with tissue transglutaminase, a crosslinking enzyme.

An iso-peptide bond is formed from peptidyl-glutamine and -lysine. In undertaking to determine which glutamines are targeted for cross-linking, Green and co-workers opted for an approach that discarded the physical problems associated with crosslinking (such as insolubility and intractability). This was done by overwhelming the natural amine donor peptidyl lysine with 14C glycine ethylester. The 14C glycine ethyl ester modified protein could be i) visualized on gels, ii) isolated by HPLC and iii) digested into a family of radioactive and nonradioactive peptides. These of course can be easily purified and sequenced. In the case of involucrin, the results obtained were most intriguing and totally unexpected. Of the 39 or so consensus repeats in intact involucrin, glutamines in only two of the repeats were consistently labeled (Simon and Green, 1988).

VpB and vpC are more degenerate in terms of repeats but they can be analogously treated with mushroom tyrosinase at pH 8.0 (phosphate buffered saline) to form messy cross-linked aggregates of high molecular weight (Waite and Rice-Ficht, 1987). Lysines are implicated in the cross-linking by two lines of evidence including i) lysine levels decrease with DOPA as the course of the oxidation proceeds, and ii) vpB is less trypsin-labile following oxidation (Waite and Rice-Ficht 1987; unpublished observation). If lysine in vpB were overwhelmed with $^{14}$C glycine ethyl ester (10 uCi, 2 mM), then in principle this protein (200 ug/50 ul) too should become increasingly labeled without necessarily becoming insoluble or resistant to trypsin. A cautionary note is advisable since other cross-links are possible. Even so, if crosslinking is limited the vpB would be digested with trypsin and tryptic peptides could be screened via C-8 reversed phase HPLC (Waite et al 1985) and liquid scintillation for 'hot' peaks. Characterization of hot peaks by amino acid analysis and microsequencing will help identify the position and number of dopaquinones targeted. There are at least four potential addition sites for glycine ethylester in peptidyl-dehydrodopaquinone.

Two additional catecholoxidases may be used in these studies: one will be extracted from the fresh byssal threads of the mussel (*Geukensia demissa*) in the following manner Byssal threads (1-23 g) are macerated then triturated by hand in a ground glass tissue grinder with two volumes of 1M NaCl, 0.05 M Tris pH 7.5, and 0.001% Triton X-100 (Waite 1985). Insolubles are removed by centrifugation (5000×G, 30 min), and the material precipitating between 10-30% (w/v) ammonium sulfate is harvested by centrifugation and redissolved in a small volume of high saline buffer. Chromatography is performed consecutively on Fractogel 55S (elution buffer=1M NaCl, 0.05 M Tris pH 7.5), Sephadex LH-60 (elution buffer=40% aqueous methanol) and Sephadex G-75 (elution buffer 0.05 M Tris and 4M urea). Enzyme is homogeneous by SDS Page and has a specific activity of 2040 units (Rzepecki and Waite 1989). Alternatively, the second enzyme may come from the vitellaria of *Fasciola hepatica*.

Example 18

Radiolabeling of Shell Proteins to Identify New Amino Acid Derivatives Resulting from Natural Crosslinking

*F. hepatica* may be labeled with radioactive isotopes corresponding to putative nucleophiles in the shell cross-linking process (cysteine, histidine and lysine) as well as with labeled tyrosine and the shell protein precursors purified. Each of the proteins will be hydrolyzed under reducing conditions as previously described for standard amino acid analysis of DOPA proteins (Waite and Rice-Ficht 1987) or reduced to amino acids enzymatically (Rice and Green 1977). New peaks on the HPLC profile will be compared with standards eluting at those positions in order to identify new species produced by crosslinking.

Example 19

Use of Bifunctional Crosslinking Agents in Combination with Monospecific Antisera to Study Protein-Protein Interactions in Shell Assembly Worms will be labeled with radioisotopes to facilitate analysis of small quantities of protein in the following studies. The label of choice will be determined by the protein which is to be analyzed. VpB is void of cysteine residues although methionine would be suitable for labeling; vpC is deficient in both sulfur containing amino acids and would be suitably labeled with glycine or arginine.

After labeling in vitro, worms will be isolated and newly-formed eggs of the distal uterus will be carefully extruded. The newly formed eggs would contain minimal native crosslinks as yet since they remain fully positive by staining with Arnow's reagent and yet this is the earliest stage in which one might expect to find the vitelline proteins in their ultimate relative positions in the shell. These immature shells may be: exposed to reversible crosslinking reagents, shell protein precursors extracted (that are not as yet trapped within the matrix), and the crosslinked species identified with a monospecific antibody. The identity may be confirmed following dissolution of the crosslink and SDS PAGE analysis.

Any choice of cross-linking reagent must be made with solubility in mind and the ease of introduction of the cross-linker into the immature shell structure; to a degree this is empirical and a number of reagents may have to be tested. An ideal cross-linking reagent for these studies considering the composition of the proteins to be crosslinked is the thiol cleavable bifunctional reagent DSP [dithiobis (succinimidyl propionate)]. Since no cysteines are present in vpB or vpC and the naturally occurring crosslinks are not labile to reducing agents, the artificially induced crosslinks will be distinguishable from the natural. This procedure has been applied to the study of protein disulfide isomerase binding to immunoglobulin (Roth and Pierce 1987) through crosslinking the proteins in vivo, immunoprecipitation of complexes with antibody directed against one protein of the complex and analysis via SDS-PAGE (reducing gel). An alternate approach using bis(imidoesters) has been applied to the study of a higher order structure, the pyruvate dehydrogenase complex of *Bacillus stearothermophilus* (Packman and Perham 1982). In analysis of these associations the cleavage step (acetonitrile and methylamine) was introduced between two dimensions of a diagonal gel electrophoresis; proteins which migrate away from the diagonal were previously cross-linked. Proteins may again be identified using antibody. The goal of the project is to analyze the proximity of the various vitelline proteins in the three-dimensional structure and to better define the role of each in shell architecture.

Example 20

Expression of Recombinant Eggshell Precursors in Prokaryotic Expression Vectors

In order to obtain enough protein for study in a form which is more soluble and manipulable, recombinant protein representing vpA, vpB and vpC will be produced in *E. coli*. The *E. coli* host does not carry enzymes to catalyze the oxidation of tyrosine and the products will be unmodified. The vector of choice for production of protein is the pGEX vector which employs the glutathione-S-transferase gene of *Schistosoma* as a purification tool (Smith and Johnson 1988). The recombinant protein will be produced as a fusion with the GST and affinity purified on glutathione-agarose beads. A proteolytic cleavage site has been introduced between the GST and the foreign protein permitting release with either factor X or thrombin. This permits a single step purification of any of the vitelline proteins followed by the release of the proteins from the GST carrier. The non-fused protein can then be employed in the studies outlined below.

Example 21

Enzymatic Oxidation of Eggshell Precursors

An analysis of the purified vitelline protein precursors reveals each of them to be post-translationally modified (tyrosine to DOPA) to a different degree. vpC is most heavily modified (100%); vpB is modified to a lesser extent (60%) and vpA contains only 30% modified tyrosine. Sequence analysis has shown that with rare exception a given tyrosine residue is modified 100% with others completely unmodified (Waite and Rice-Ficht 1992). The basis for this modification is uncertain since there appears to be no absolute consensus sequence flanking the modified residues. Recombinant protein will be enzymatically modified to varying degrees in vitro (Waite and Rice-Ficht 1987) and specific tryptic peptides analyzed for DOPA composition.

Example 22

Production of Polyvalent and Monoclonal Antibody for Fine Structure Localization of Proteins Involved in Shell Production The production of antibody directed against specific vitelline proteins has in the past proved problematic; the problems are based on: i) an apparent lack of antigenicity of the proteins; and ii) antibody raised against the proteins is often directed to the DOPA moieties producing a cross-reacting antisera. To manufacture reagents specific for each protein we propose to inoculate rabbits (for polyspecific sera) and mice (for monoclonal antibody) with denatured recombinant protein representing each of the vitelline proteins in RIBI's adjuvant. The rationale is to raise antibody against the primary sequence of the proteins which will be useful in distinguishing proteins in Western blot or fixed, embedded tissue (i.e. in a denatured state). High titer sera directed specifically against vpB and one monoclonal antibody specific to vpB have been generated; in order to probe different epitopes of vpB, vpC or vpA, additional reagents may be required. Shell precursors and enzymes in the vitelline globules may be visualized through transmission EM and immunogold tagging. The localization of each protein to each phase of the vitelline globule is critical to the understanding of how emulsions of the proteins are formed and later combined prior to quinone tanning.

Example 23

Coacervation Produced Capsules Containing vpB

Capsules composed of vpB ranging from 5 to 200 microns in size were produced through coacervation technology as follows: 200 µl of phosphate buffered saline solution, pH 7.2, containing 2 mg recombinant vpB and 2 mg recombinant proline-rich protein from *F. hepatica* was vortexed; 240 µl of 2-isopropanol (coacervating agent) was added dropwise while vortexing. As mixing continued, 60 ml of sodium sulfate solution (30% by weight sodium sulfate in $dH_2O$) was added dropwise. Fixation was achieved by addition of 54 μl of formaldehyde solution (37% in $dH_2O$) while mixing for 10 minutes.

Example 24

Protein Microspheres Produced Through Oil in Water Emulsion Technology

Encapsulation and release of small molecules, entrapment of tritiated glycine. Protein microspheres were produced using the following formulation: Microspheres were produced as a composite between bovine serum albumin (Fraction V, Sigma Chemicals) and recombinant vpB. 100 ml of olive oil is stirred for 30 minutes in a 400 ml beaker using a Caframo ultra high torque stirrer at a speed at 1200 rpm (300-1800 rpm) specific for the size of capsule to be produced. Then 2 ml of a 126 mg/ml protein solution containing bovine serum albumin (125 mg) and vpB (1 mg) and a compound to be dispersed (1.25 mg glycine; 30 microcuries [$^3$H] glycine) was added to the oil and the stirring continued for 30 minutes at 1200 rpm. Aqueous droplets of protein in the emulsion were crosslinked through the addition of 50 microliters of 37% formaldehyde (or glutaraldehyde 0.1-25%) followed by stirring for an additional 15-30 minutes. Glycine, a capping agent for aldehyde groups, was then added (125 mg/ml, 50 microliters of a 125 mg/ml solution in phosphate buffered saline) and the emulsion stirred for an additional 15 minutes. Microspheres were then collected through centrifugation (10 minutes, 2400 rpm, Beckman TH-4 centrifuge) and the microspheres washed in ether (twice in 20 ml diethyl ether) to remove residual oil. Size is determined by oil viscosity, stirring speed and surface properties of the encapsulant.

Release of [$^3$H] glycine was determined by rocking the microcarriers in a solution of phosphate buffered saline (PBS) or in PBS:bovine serum (50:1). Samples were taken throughout a 72 hour period and analyzed through liquid scintillation (P. Baukudumbi, K. H. Carson, A. C. Rice-Ficht and M. J. Andrews, on the diameter and size distribution of bovine serum albumin (BSA) microspheres, Journal of Microencapsulation (2004)). As shown in FIG. 2, it was found that using the present invention the release of a small molecule, [$^3$H] glycine, was delayed for up to eight hours with 72-75% released by that time point. The remaining 25% was released over 72 hours.

Example 26

VpB/Albumin Protein Microsphere Utility as a Vaccine Delivery Vehicle for Extended or Controlled Release of Tetanus Toxoid Fragment Microcarriers produced through the same emulsion formulation as described for glycine entrapment were utilized in the following studies. Groups of six mice were treated via subcutaneous injection of encapsulated tetanus toxoid (TT; 10 micrograms per dose) manufactured with oil in water emulsion technology (above). Composite capsules contained the following: 74% albumin:26% vpB. A second group of capsules were bovine serum albumin loaded with TT (99.99% bovine serum albumin; 10 micrograms TT) and composite (vpB/albumin) loaded with TT (10 micrograms/dose).

The vpB microencapsulating additive was also used to entrap tetanus toxoid for the above studies. Capsules were introduced subcutaneously as a depot and serum antibody titers monitored for a period of weeks using enzyme linked immunosorbent assay_ELISA (FIG. 3). Use of 26% vpB in the composite capsule formulation resulted in an extended period of elevated serum antibody response to tetanus toxoid, at week 11 a level more than 10 fold that of TT loaded albumin capsules was observed.

Example 27

VpB/albumin protein microsphere utility as a vaccine delivery vehicle for botulinum toxin fragment. Microcarriers produced through the same emulsion formulation as described for glycine entrapment.

FIG. 4 is a graph that shows the results of botulinum toxin encapsulated using the present invention and delivered as a depot. Serum antibody titers for mice determined over a period of 17 weeks are shown. Groups of 6 mice were analyzed. Results are from pooled sera.

The hallmark of the composite capsule is the slow erosion and the extended release profile (group 4C) when delivered as a subcutaneous depot. Botulinum neurotoxin A (recombinant fragment C) was delivered as a subcutaneous depot in: free form (5C, 2 micrograms per dose), and encapsulated in protein (1C-4C). 4C is a 10 micron composite capsule with 3% vpB; 97% bovine serum albumin; 2 micrograms Bot toxin). Serum antibody response with this capsule formulation is retained at 17 weeks. This is superior to the delivery of the toxin in a free form which directs a high serum antibody response at 5 weeks that diminishes sharply at 7 weeks.

Example 28

Figure 5:
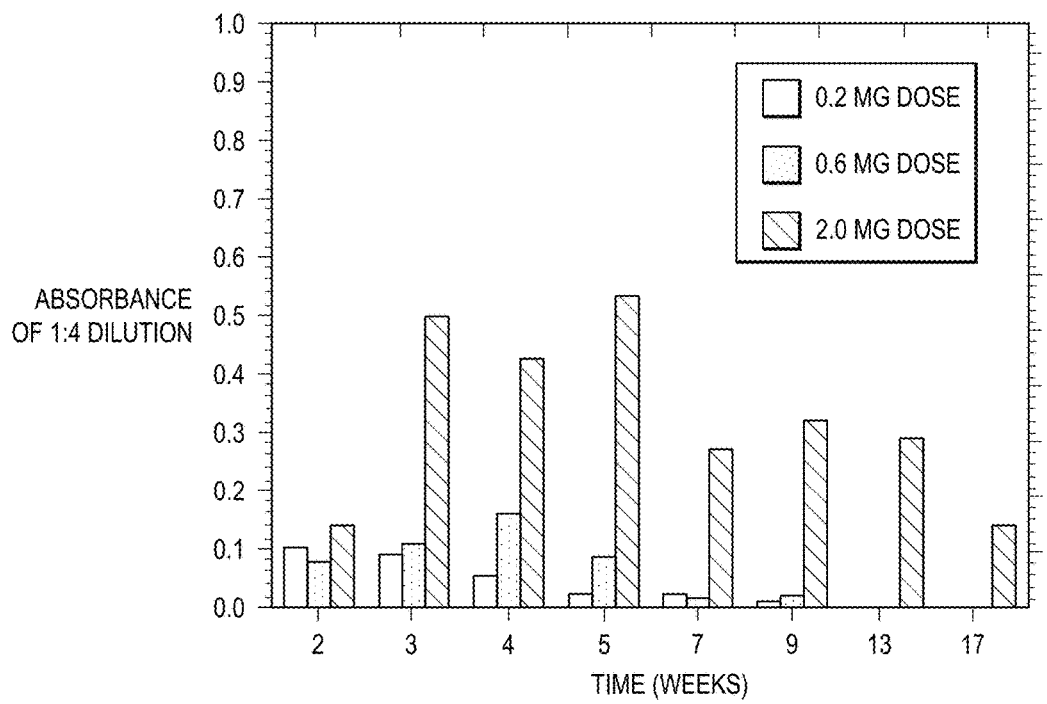
FIG. 5 is a graph that shows the immune response to doses of botulinum neurotoxin A, fragment C trapped in the composite capsule was dose dependent.

Dose Dependence of the Serum Antibody Response to Encapsulated Botulinum Toxin Fragment C FIG. 5 is a graph that shows the immune response to doses of botulinum neurotoxin A, fragment C trapped in the composite capsule described above, were dose dependent. The batches of capsules are identified by dose referring to the mg dose of capsule. The capsule doses in milligrams contain the following doses of bot tox: 0.2 mg-0.2 micrograms of toxin; 0.6 mg-0.6 micrograms of toxin; 2.0 mg-2.0 micrograms of toxin. Individual animals received 2 micrograms per dose. Results indicate that vpB albumin composite capsules carrying a 2.0 mg dose of capsule induce serum antibody titers at substantially extended times when compared to lower doses of botulinum neurotoxin A, fragment C.

Example 29

Figure 6:
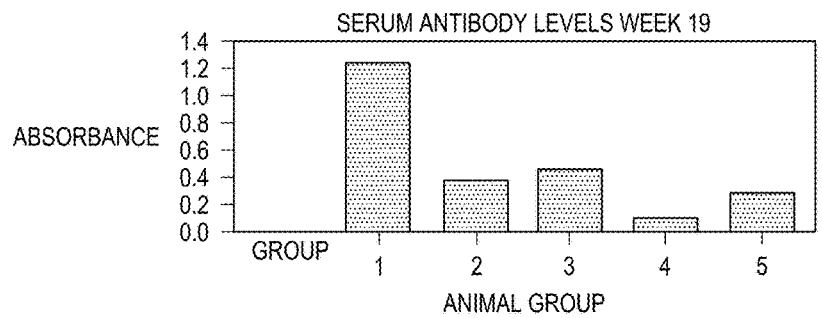
FIG. 6 is a graph that shows the antibody response of six mice injected subcutaneously with encapsulated TT (tetanus toxoid) composite capsules.

Emulsion Capsules Used to Entrap Tetanous Toxoid and Deliver Vaccine Through a Combination of Subcutaneous/Oral Routes to Mice FIG. 6 is a graph that shows the antibody response of six mice injected subcutaneously with encapsulated TT composite capsules. Capsules were produced through emulsion technology described above entrapping tetanus toxoid (TT, 100 micrograms per dose). Groups of six mice were injected subcutaneously with encapsulated TT composite capsules (tetanous toxoid 10 micrograms per milligram of formulation/bovine serum albumin 95%/recombinant vpB 5%, G1), albumin/TT (bovine serum albumin 99.99%, tetanus toxoid 10 micrograms per milligram of formulation G2), empty composite capsule (bovine serum albumin 95%/recombinant vpB 5%, G3), tetanus toxoid unencapsulated, 100 micrograms (G4) and saline (G5). Dosing was performed as follows: Groups 1-3 received: 10 mg of specified capsule formulation (containing TT 100 micrograms) delivered subcutaneously at time 0. Mice were boosted orally at weeks 3 and 6 with 10 mg of specified formulation in 250 microliters of corn oil and buffer (1:1). Group 4 received 100 micrograms of unencapsulated TT at time 0 and was boosted at 3 and 6 weeks orally with 100 micrograms TT in 250 microliters of corn oil:buffer (1:1). Group 5 received no treatment Sera were pooled for analysis and serum antibody measured through ELISA using tetanus toxoid as antigen. Secondary antibody detected IgG. Results indicate that the composite formulation which contains vpB at a level of 5% and tetanus toxoid as antigen results in an extended presentation of antigen to the immune system and a higher serum antibody level (3 fold) at extended times when compared with a control empty composite capsule (G3). Parallel studies with doses of 200 micrograms of tetanus toxoid revealed similar results.

Figure 7:
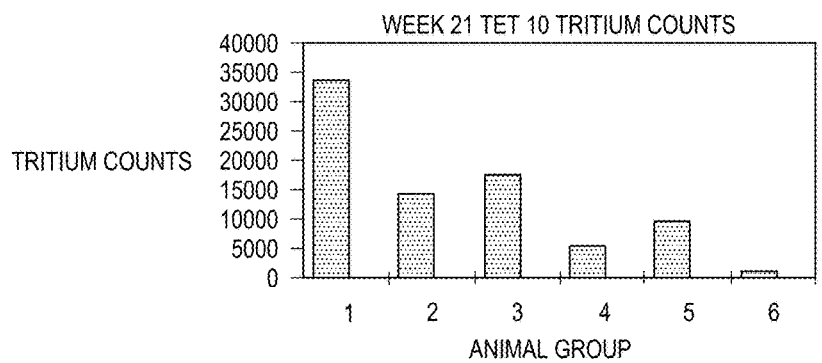
FIG. 7 is a graph that shows cellular immune response as measured by tritium uptake for the same groups as FIG. 6 at 21 weeks.

FIG. 7 is a graph that shows cellular immune response as measured by tritium uptake for the same groups as FIG. 6 at 21 weeks. Splenocyte blastogenesis from the same mice at the conclusion of the studies indicated that a strong cell mediated response had also been obtained when utilizing vpB as an additive (group 1).

Example 30

Assay for the Adhesive Properties of Vitelline B Protein

Vitelline B protein (4 mg) can be dissolved in 150 ml of Phosphate Buffered Saline (PBS-10 mM phosphate, 120 mM NaCl, pH 7.4) or 150 ml of 5 M Guanidinium HCl. This solution can be combined with an equal volume of 30% hydrogen peroxide (25 ml of each). The solution can be placed between the surfaces to be adhered to one another, and placed in a 45° C. oven overnight in order to cure.

Other chemical oxidants can also be used including chemicals, enzymes, such as mushroom tyrosinase, and buffers with extreme pH to convert tyrosine in the vpB recombinant protein to DOPA and DOPA quinone and impart sticky properties to the protein. The use of a denaturant is optional, and others such as urea can be used in place of guanidinium hydrochloride. General methods for making proteins adhesives are taught Hwang, D. S., Yoo, H. J., Moon, W. K., and Cha, H. J. (2004) Applied and Environ. Micro. 70, 3352-3359, relevant portions incorporated herein by reference.

Example 31

Alginate-vpB Composite Capsules for Vaccination with Live *Brucella abortus*

Capsule design 1: Bacteria $1\times10^4$-$1\times10^{10}$ were suspended in 2 ml phosphate buffered saline and mixed with 10 ml of a 1.5% alginate solution in a 60 ml syringe. The syringe was attached to the inflow port of an Encapsulator device (Inotech, Inc.) and delivered dropwise through a nozzle of defined aperture (50-700 microns) into a $CaCl_2$ bath (10 mM $CaCl_2$, 225 ml). Beads thus formed were incubated with stirring for 5 minutes. $CaCl_2$ was withdrawn and a solution of either 0.05% poly-L-lysine or 0.05% poly-L-lysine in $CaCl_2$ was added along with 0.0625-1 mg of vpB protein. This solution was stirred for 10 minutes and withdrawn. The capsules were then washed once for 1 minute with 100 ml MOPS buffer, then once for 5 minutes with 150 ml MOPS buffer. The MOPS buffer was withdrawn and 100 ml of a 0.03% solution of alginate was added to the beads and stirred for 5 minutes. Alginate was again withdrawn and the capsules washed with 100 ml MOPS buffer for 1 minute, drained and washed with an additional 150 ml MOPS buffer for 5 minutes. Capsules were collected and stored in MOPS buffer at 4° C.

Capsule design 2: Alternatively, the vpB protein, at the same concentrations indicated in capsule 1, was included with the alginate and bacteria along with the contents of the syringe and dropped into the $CaCl_2$ solution. In this embodiment the vpB was not included in the 'shell', but as component of the core. Both applications were tested in mice.

Figure 8:
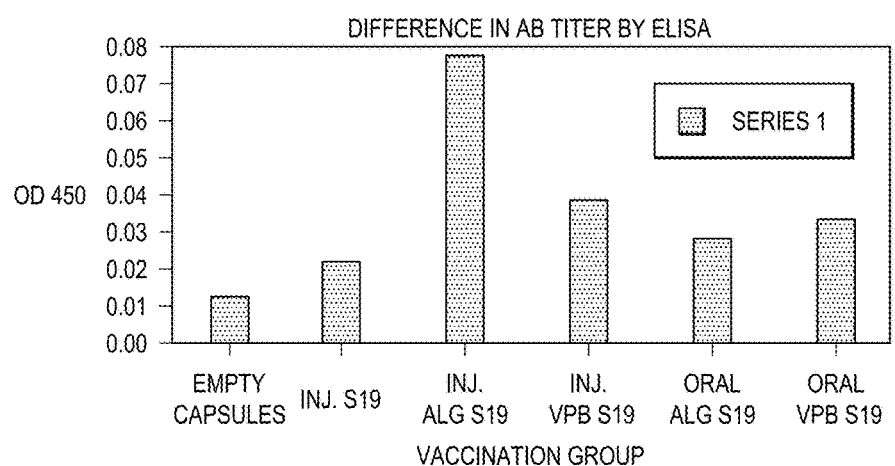
FIG. 8 is a graph that shows the results obtained from Red deer vaccination studies.

FIG. 8 is a graph that shows the results obtained from red deer vaccination studies conducted with capsule design 1 only using the following approach: Groups of 4 red deer were vaccinated orally or subcutaneously with alginate or alginate composite capsules containing entrapped live *Brucella abortus* vaccine. Animals were bled prior to commencement of the study for baseline serum titers Animals were vaccinated on day 1 and boosted with the same dose and formulation at 4 weeks. Animals were challenged with the vaccine strain on week 7 and sacrificed at week 14. The vaccination groups are as follows: empty composite capsules (subcutaneous), unencapsulated vaccine strain S19 (injected), alginate encapsulated vaccine strain (injected), composite encapsulated vaccine strain (injected), encapsulated vaccine strain (oral), composite encapsulated vaccine strain (oral). Each animal received a dose of $7\times10^9$-$1\times10^{10}$ organisms per dose. The results of this study are indicated below.

Serum IgG titers of red deer at week 11 indicate that encapsulated forms of delivery out perform the unencapsulated vaccine with respect to maintenance of serum antibody titer. At 11 weeks the titer of animals vaccinated with composite capsules was lower than that of alginate alone while the orally dosed animals showed higher titers with composite capsules that those encapsulated with alginate alone.

Figure 9:
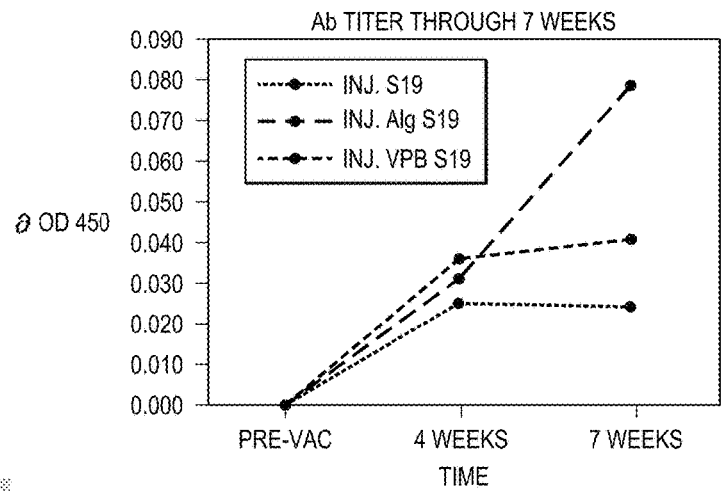
FIG. 9 is a graph that shows the kinetics of humoral immunity with subcutaneous vaccination of the present invention.

FIG. 9 is a graph that shows the kinetics of the induction of humoral immunity as a result of subcutaneous vaccination. Although the titers of animals receiving unencapsulated S19 are falling at 7 weeks, that of both encapsulated forms is rising. The alginate encapsulated vaccine is producing a steep increase in titer at 4 and 7 weeks. The composite alginate/vpB encapsulated vaccine is rising at a slower rate providing a lower level, longer term release of the vaccine. Therefore, longer term release was made possible by the inclusion of the vpB protein additive of the present invention, possibly due to its slow decomposition enhancing the performance of capsules in extended release.

Example 32

Figure 10:
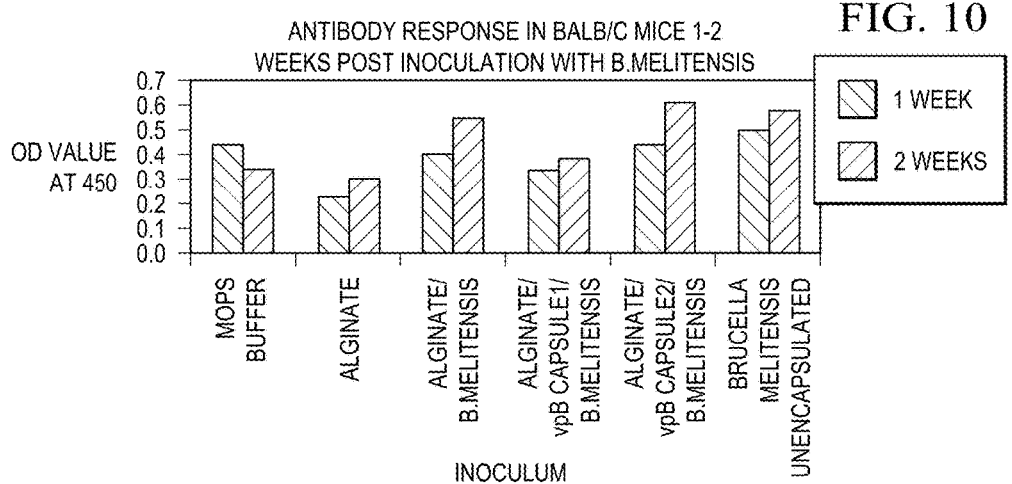
FIG. 10 is a graph of serum antibody levels in *Brucella melitensis* immunized mice.

Alginate-vpB Composite Capsules for Vaccination with Live *Brucella melitensis* in Mice To determine the utility of vpB in composite capsules the present inventors used capsule design 1 and 2 in the delivery of an attenuated *Brucella melitensis* strain to mice. All animals except group 1 received an innoculum of $1\times10^5$ organisms through intraperitoneal injection at the initiation of the study. Serum antibody titers have been monitored weekly over a three week period following vaccination. The groups as summarized in Table 2. The results are shown in FIG. 10. Improved antibody titers against the live vaccine strain are seen with the use of capsule formulation #2, in which vpB is included with the alginate core and with the vaccine strain. It is predicted that vpB containing formulation will experience extended serum antibody titers and enhanced protection over other methods. Alginate capsules, which do not contain any vpB additive, failed to produce antibody titers as elevated as those of vpB containing alginate capsules.

TABLE 2

Intraperitoneal Injection of *Brucella melitensis* in mice

| INOCULUM | Group # | Dose | Organisms per dose | Number of animals per group |
|---|---|---|---|---|
| MOPS buffer | 1 | 0.1 ml | $10^5$ | 10 |
| Alginate | 2 | 0.1 ml | $10^5$ | 10 |
| Alginate/*Brucella mellitensis*(2*) | 3 | 0.1 ml | $10^5$ | 10 |
| Alginate/vpB capsule 1/ *Brucella melitensis*(1*) | 4 | 0.1 ml | $10^5$ | 10 |
| Alginate/vpB capsule 2/ *Brucella melitensis*(3*) | 5 | 0.1 ml | $10^5$ | 10 |
| *Brucella melitensis* unencapsulated | 6 | 0.1 ml | $10^5$ | 10 |

Example 33

Alginate-vpB Capsules for Controlled Release of an Active Protein, Interferon tau Capsule design 1 was used as follows. Interferon tau (from Dr. Fuller Baser, Dept Animal Science, TAMU) 1 ml ($10^8$ units) was suspended in 1 ml MOPS buffer and mixed with 5 ml of a 1.5% alginate solution in a 60 ml syringe. The syringe was attached to the inflow port of an Encapsulator device (Inotech, Inc.) and delivered dropwise through a nozzle of defined aperture (50-700 microns) into a 10 mM $CaCl_2$ bath (225 ml). Beads thus formed were incubated with stirring for 5 minutes. $CaCl_2$ was withdrawn and a solution of either 0.05% poly-L-lysine or 0.05% poly-L-lysine in $CaCl_2$ was added in combination with 0.0625-1 mg of vpB protein. This solution was stirred for 10 minutes and withdrawn. The capsules were then washed once for 1 minute with 100 ml MOPS buffer, then once for 5 minutes with 150 ml MOPS buffer. The MOPS buffer was withdrawn and 100 ml of a 0.03% solution of alginate was added to the beads and stirred for 5 minutes. Alginate was again withdrawn and the capsules washed with 100 ml MOPS buffer for 1 minute, drained and washed with an additional 150 ml MOPS buffer for 5 minutes. Capsules were collected and stored in MOPS buffer at 4° C.

Encapsulated interferon tau was delivered to mice as a treatment regimen for virally induced neurodegenerative disease. Capsules of 400 microns in diameter containing a dose of $2 \times 10^6$ units were delivered through intraperitoneal injection.

SJL mice were infected with $5 \times 10^4$ pfu BeAn strain of Theiler's virus or mock infected with PBS. The mice were assigned to one of the following groups (10 mice per group) described in Table 3 below. The dose IFN will be $10^5$ units i.p. which has been shown to be effective in the treatment of TVID as summarized in Table 3.

TABLE 3

Results from Study Groups

| Group | Infection | Treatment | Route of Treatment | Timing of Treatment |
|---|---|---|---|---|
| A | + | IFN-τ | i.p | Daily |
| B | + | IFN-τ | oral | Daily |
| C | + | Saline | i.p | Daily |
| D | + | IFN-τ | i.p. | Twice weekly |
| E | + | IFN-τ | oral | Twice weekly |
| F | + | Saline | i.p. | Twice weekly |
| G | + | Saline | oral | Twice weekly |
| H | − | IFN-τ | i.p. | Daily |
| I | − | IFN-τ | oral | Daily |
| J | + | Encapsulated IFNt | i.p. | Once biweekly |

The mice have been weighed and evaluated for clinical signs of disease at weekly intervals. Mice treated with encapsulated INFt shown clinical improvement comparable to that of mice receiving daily intraperitoneal doses. The delivery of a dose of encapsulated INFt serves to reduce the treatment regimen from once daily to once every 2 weeks.

Figure 11:
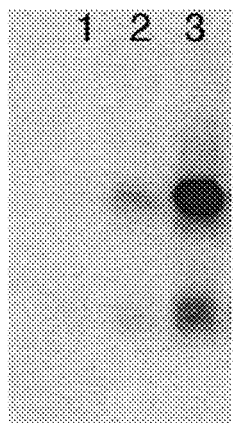
FIG. 11 shows the fluorescence profile of green fluorescent protein released over a one week period as determined through SDS polyacrylamide gel electrophoresis and fluorescence analysis. Lane 1 illustrates green fluorescent protein (gfp) released from an alginate capsule type 1 in 3 hours, lane 2, 24 hours and lane 3, 7 days.

Controlled release of a model protein, green fluorescent protein, from capsules of type one design have been carried out by loading of capsules during manufacture and monitor of release kinetics over a two week period. Results indicate release of only 5-6% of the protein within twenty four (24) hours and sustained release of the protein over a 10 day period from capsules of type one design. FIG. 11 shows the fluorescence profile of the gfp released over a one week period as determined through SDS polyacrylamide gel electrophoresis and fluorescence analysis. Lane 1 illustrates gfp released from an alginate capsule type 1 in 3 hours, lane 2, 24 hours and lane 3, 7 days. Release in a 24 hour period is approximately 5-6% of the total encapsulated protein. The gfp protein is the approximate molecular weight of interferon tau and illustrates the predicted release profile of a similar protein from this type of capsule.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims. All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

1. Arnow, L. E. (1937) J. Biol. Chem. 118, 531-537.
2. Bahukudumbi, P., Carson, K. H., Rice-Ficht, A. C., and Andrews, M. J. (2004) On the diameter and size distributions of bovine serum albumin (BSA)-based microspheres. J. Microencapsulation (in press).
3. Bouligand, Y. and Girard-Guille, M.-M. (1985) in Biology of Invertebrate and Lower Invertebrate Collagens. Bairati, A. & Garrone, R., eds., Plenum Press, New York p. 115-134.
4. Bordier, C. (1981) J. Biol. Chem. 256, 1604-1607.
5. Clegg, J. A. (1965) Annals N.Y. Acad. Sci. 118, 969-986.
6. Degrand, C. (1985) Annal. Chim. 75, 1-18.
7. Dohmoto, N. and Miyachi, S. (1991) Intern. Mar. Biotechnol. Conf., P18 (abstract).
8. Duckworth, H., & Coleman, J. E. (1970) J. Biol. Chem. 245, 1613-1623.
9. Eckert, R. L. and Green, H. (1986) Cell 46, 583-589.
10. Fried, B. (1989) Parasitology Today 5, 3-4.
11. Gyllensten, U. B. and Erlich, H. A. (1988) Proc. Natl. Acad. Sci. U.S.A. 85, 7652-7656.
12. Hall, T. A. (1979) J. of Microscopy 117, 145-163.
13. Hedrick, S. M., Cohen, D. I., Nielsen, E. A. and Davis, M. M. (1984) Nature 308, 149-153.
14. Hwang, D. S., Yoo, H. J., Moon, W. K., and Cha, H. J. (2004) Applied and Environ. Micro. 70, 3352-3359.
15. Jaegfeldt, H., Kuwana, T. and Johansson, G. (1983) JACS 105, 1805-1814.
16. Jones, S. M., Mu, D., Wemmer, D., Smith, A. J., Kaur, S., Maltby, D., Burlingame, A. M. and Klimman, J. P. (1990) Science 248, 981-987.
17. Kurelec, B. (1972) Compo Biochem. Physiol. 43B, 769-780.
18. Lamar, E. E. and Palmer, E. (1984) Cell 37, 171-177.
19. Lau, A. N. K. and Miller, L. L. (1983) JACS 105, 5271-5277.
20. Mansour, T. E. (1958) Biochim. Biophys. Acta 30, 492-500.

21. Nellaiappan, K. and Ramalingam, K. (1980) Molec. Biochem. Parasitol. 2, 109-112.
22. Ohtsuka, E., Matsuki, 5., Ikehara, M., Takahashi, Y. and MatsubarA, K. (1985) J. Biol. Chem. 260, 2605-2608.
23. Ong, S. A., Peterson, T. and Neilands, J. B. (1979) J.B.C. 254, 1860-1865.
24. Ozols, J. (1986) J. Biol. Chem. 261, 3965-3979.
25. Packman, L. C. and Perham, R. N. (1982) Biochemistry 21, 5171-5175.
26. Pecoraro, V. L., Weitl, F. L. and Raymond, K. N. (1981) JACS 103, 5133-5140.
27. Pizzi, A. (1985) Polym. Mat. Sci. Eng. 52, 251-255.
28. Raymond, K. N. and Carrano, C. J. (1979) Acc. Chem. Res. 12, 173-190.
29. Reis, M. G., Kuhns, J., Blanton, R. and Davis, A. H. (1989) Mol. Biochem. Parasit. 32, 113-120.
30. Rice, R. H. and Green, H. (1977) Vrll 11, 417-422.
31. Rice-Ficht, A. C., Dusek, K. A., Kochevar, G. J. and Waite, J. H. (1992) II. Eggshell Precursor Proteins of *Fasciola hepatica*: Structure and Expression of Vitelline Protein B. Molecular and Biochemical Parasitology, 54, 143-152.
32. Rice-Ficht, A. C. (1992) Composition and Design of *Fasciola hepatica* Eggshells. In "Results and Problems in Cell Differentiation: Structure, Cellular Synthesis and Assembly of Biopolymers". (S.T. Case, ed.) Springer-Verlag, Heidelberg, Chapter 4, pp. 75-95.
33. Richards, A. G. (1978) in Biochemistry of Insects. Rockstein R., Ed., Academic Press, Inc. New York. p. 205-232.
34. Roth, R. A. and Pierce, S. B. (1987) Biochemistry 26, 4179-4182.
35. Rzepecki, L. and Waite, J. H. (1989) Anal. Biochem. 179, 375-381.
36. Sanchez-Ferrer, A., Vilalba, J., Garcia-Carmona, F. (1989) Phytochemistry 28, 1321-1325.
37. Sanger, F. and Coulson, A. R. (1975) J. Mol. Biol. 94, 441-448.
38. Schaefer, J., Kramer, K. J., Garbow, J. R., Jacob, G. S. Stejskal, E. 0.,
39. Hopkins, T. L. and Speirs, R. D. (1987) Science 235, 1200-1204.
40. Seed, J. L. and Bennett, J. L. (1980) Exp. Parasitol. 49, 430-441.
41. Seed, J. L., Boff, M. and Bennett, J. L. (1978) J. Parasitol. 64, 283-289.
42. Segel, I. (1976) Biochemical Calculations. Wiley, New York, p. 111-116.
43. Shaw, M. K. and Erasmus, D. A. (1984) Experimental Parasit. 58, 163-181.
44. Simon, M., and Green, H. (1988) J. Biol. Chem. 263, 18093-18098.
45. Smith, R. B. and Johnson, K. S. (1988) Gene 67, 31.
46. Smyth, J. D. (1954) Quart. J. Micros Sci. 95, 139-152.
47. Smyth, J. D. and Clegg, J. (1959) Exp. Parasitol. 8, 286-323.
48. Tedder, T. F., Strueli, M., Schlossman, S. F. and Saito, H. (1988) Proc. Natl. Acad. Sci. U.S.A. 85, 208-212.
49. Thangaraj, T., Vinayaka, A. and Nelaiappan, K. (1986) J. Helminthology 60, 234-238.
50. Tsugita, A., Uchida, T., Mewes, H. W. and Ataka, T. (1987) J. Biochem. 102, 1593-1597.
51. Waite, J. H. and Tanzer, M. L. (1980) Science 212, 1038-1040.
52. Waite, J. H. (1985) J. Mar. Biol. Assoc. UK 65, 359-371.
53. Waite, J. H., Housley, T. J. and Tanzer, M. L. (1985) Biochem. 24, 5010-5015.
54. Waite, J. H. (1986) J. Compo Physiol. B. 156, 491-496.
55. Waite, J. H. and Rice-Ficht, A. C. (1987) Biochemistry 26, 7819-7825.
56. Waite, J. H. and Rice-Ficht. A. C. (1989) Biochemistry 28, 6104-6110.
57. Waite, J. H. and Rice-Ficht, A. C. (1990) Appendix I. (prepared for submission to Molecular and Biochemistry Parasitology)
58. Waite, J. H. and Rice-Ficht, A. C. (1992) I. Eggshell Precursor Proteins of *Fasciola hepatica*: Microheterogeneity in Vitelline Protein B. Molecular and Biochemical Parasitology, 54, 129-142.
59. Wang, et al. (1986) Molec. Biochem. Parasitol. 18, 69-72.
60. Wharton, D. A. (1983) Parasitology 86, 85-97.
61. Wood, W. I., Gitschier, J., Laskey, L. A. and Lawn, R. M. (1985) Proc. Natl. Acad. Sci. U.S.A. 82, 1585-1588.
62. Young, R. A. and Davis, R. W. (1983) Proc. Natl. Acad. Sci. U.S.A. 80, 1194-1198.
63. Zurita, M., Bieber, D., Ringold, G. and Mansour, T. E. (1987) Proc. Natl. Acad. Sci. USA 84, 2340-2344.

What is claimed is:

1. A method of making an extended release formulation comprising:
   providing a recombinant scrambled vitelline protein B (vpB) peptide which retains the same amino acid ratio as the ratio of amino acids 82-187 of the amino acid sequence selected from the group consisting of SEQ ID NO:1 and SEQ ID NO:2;
   combining the recombinant scrambled peptide, one or more active agents, a crosslinking agent and an alginate; and
   crosslinking the recombinant scrambled peptide, the one or more active agents, the crosslinking agent and the alginate to form the extended release formulation.

2. The method of claim 1, wherein the one or more active agents are released for between about 1 hour to about 8 hours, or between about 1 hour to about 2 weeks, or between about 1 hour to about 6 months.

3. The method of claim 1, wherein the one or more active agents comprise a pharmaceutical agent, an enzyme, a cytokine, a growth promoting agent, an antibody, an antigen, a vaccine, a cell, a live-attenuated pathogen, a heat-killed pathogen, a virus, a bacteria, a fungi, a peptide, a protein, a carbohydrate, a nucleic acid, a lipid, mixtures and combinations thereof.

4. The method of claim 1, wherein the one or more active agents, and the alginate are combined with the cross-linking agent and the peptide by coacervation, spray freezing, extrusion, nebulization, spray drying or into liposomes.

5. The method of claim 1, wherein the crosslinking agent is poly-L Lysine and the ratio of the poly-L lysine to the peptide is between 30:70 to 70:30 weight to weight.

6. The method of claim 1, wherein the crosslinking agent is poly-L Lysine and the ratio of the poly-L lysine to the peptide is between about 50:50 weight to weight.

7. The method of claim 1, wherein the crosslinking agent is a cation or a polycation.

8. The method of claim 1, wherein the one or more active agents is an antigen and the antigen comprises *Brucella* sp.

9. The method of claim 1, wherein the method further comprises the step of lyophilizing the composition.

10. A method of making an extended release formulation comprising:
    providing a recombinant scrambled vitelline protein B (vpB) peptide which retains the same amino acid ratio as the ratio of amino acids in a central 33% portion of the amino acid sequence selected from the group consisting of SEQ ID NO:1 and SEQ ID NO:2;
    combining the recombinant scrambled peptide, a poly-Lysine crosslinking agent, one or more active agents and an alginate to form a release formulation, wherein the ratio of the peptide to the poly-Lysine crosslinking agent is between 30:70 to 70:30 weight to weight; and
    crosslinking the recombinant scrambled peptide, the poly-Lysine crosslinking agent, the one or more active agents and the alginate to form the extended release formulation.

11. The method of claim 10, wherein the crosslinking agent is poly-L Lysine.

* * * * *

UNITED STATES PATENT AND TRADEMARK OFFICE
CERTIFICATE OF CORRECTION

PATENT NO. : 9,555,073 B2
APPLICATION NO. : 13/407427
DATED : January 31, 2017
INVENTOR(S) : Allison R. Ficht et al.

Page 1 of 1

It is certified that error appears in the above-identified patent and that said Letters Patent is hereby corrected as shown below:

In the Specification

Column 1, Lines 15-25 should be replaced with:
STATEMENT REGARDING FEDERALLY SPONSORED RESEARCH
This invention was made with government support under contract numbers DAMD17-95-C-5048 and W81XWH-10-1-0255 awarded by the U.S. Army Medical Research and Materiel Command, grant number NCC-1-02038 awarded by the National Aeronautics and Space Administration, and contract number 0300125 awarded by the US Geological Survey. The government has certain rights in the invention.

Signed and Sealed this
Tenth Day of July, 2018

Andrei Iancu
*Director of the United States Patent and Trademark Office*